United States Patent
Verdine et al.

(10) Patent No.: US 6,183,965 B1
(45) Date of Patent: Feb. 6, 2001

(54) SYNTHETIC TRANSCRIPTIONAL MODULATORS AND USES THEREOF

(75) Inventors: Gregory L. Verdine, Lexington, MA (US); Origene Nyanguile, Gaithersburg, MD (US)

(73) Assignee: President and Fellows of Harvard College, Cambridge, MA (US)

( * ) Notice: Under 35 U.S.C. 154(b), the term of this patent shall be extended for 0 days.

(21) Appl. No.: 09/208,057

(22) Filed: Dec. 9, 1998

Related U.S. Application Data

(63) Continuation-in-part of application No. 08/987,912, filed on Dec. 9, 1997.

(51) Int. Cl.[7] .................................................. C12Q 1/68

(52) U.S. Cl. ............................ 435/6; 435/325; 435/372.3

(58) Field of Search ............................. 435/6, 325, 372.3

(56) References Cited

U.S. PATENT DOCUMENTS 5,468,614 * 11/1995 Fields et al. ............................... 435/6

FOREIGN PATENT DOCUMENTS

| | | |
|---|---|---|
| WO 91/01379 | 2/1991 | (WO) . |
| WO 94/18317 | 8/1994 | (WO) . |
| WO 95/02684 | 1/1995 | (WO) . |
| WO 96/06110 | 2/1996 | (WO) . |
| WO 96/06111 | 2/1996 | (WO) . |
| WO 96/41865 | 12/1996 | (WO) . |
| WO 96/01313 | 1/1997 | (WO) . |

OTHER PUBLICATIONS

Arany, Z. et al., "A Family of Transcriptional Adaptor Proteins Targeted by the E1A Oncoprotein," *Nature*, vol. 374, 81–4 (1995).

Belshaw, P. et al., "Controlling Protein Association and Subcellular Localization with a Synthetic Ligand that Induces Heterodimerization of Proteins," *PNAS*, vol. 93, 4604–7(1996).

Bierer, B. et al., "Probing Immunosuppressant Action with a Nonnatural Immunophilin Ligand," *Science*, vol. 250, 556–9 (1990).

Bierer, B. et al., "Two Distinct Signal Transmission Pathways in T Lymphocytes are Inhibited by Complexes Formed Between an Immunophilin and Either FK506 or Rapamycin," *PNAS*, vol. 87, 9231–5 (1990).

Chen, J. et al., "Identification of an 11–kDa FKBP12–rapamycin–binding Domain Within the 289–kDa FKBP12–rapamycin–associated Protein and Characterization of a Critical Serine Residue," *PNAS*, vol. 92, 4947–51 (1995).

Clackson, T., "Controlling Mammalian Gene Expression with Small Molecules," *Current Opinion in Chemical Biology*, vol. 1, 210–8 (1997).

Gallop, M. et al., "Applications of Combinatorial Technologies to Drug Discovery. 1. Background and Peptide Combinatorial Libraries," *Journal of Medicinal Chemistry*, vol. 37, No. 9, 1233–51 (1994).

Gottesfeld, J. et al., "Regulation of Gene Expression by Small Molecules," *Nature*, vol. 387, 202–5 (1997).

Ho, S. et al., "Dimeric Ligands Define a Role for Transcriptional Activation Domains in Reinitiation," *Nature*, vol. 382, 822–6 (1996).

Jenster, G. et al., "Steroid Receptor Induction of Gene Transcription: A Two–step Model," *PNAS*, vol. 94, 7879–84 (1997).

Kay, J. "Structure–function Relationships in the FK506–binding Protein (FKBP) Family of Peptidylprolyl cis–trans Isomerases," *Biochem. J.*, vol. 314, 361–85 (1996).

Ma, J. and Ptashne, M., "A New Class of Yeast Transcriptional Activators," *Cell*, vol. 51, 113–9 (1987).

Ossareh–Nezari, B. et al., "Evidence for a Role of CRM1 in Signal–Mediated Nuclear Protein Export," *Science*, vol. 278, 141–4 (1997).

Owen–Hughes, T. and Workman, J., "Remodeling the Chromatin Structure of a Nucleosome Array by Transcription Factor–targeted trans–displacement of Histones," *The EMBO Journal*, vol. 15, No. 17, 4702–12 (1996).

Rivera, V. et al., "A Humanized System for Pharmacologic Control of Gene Expression," *Nature Medicine*, vol. 2, No. 9, 1028–32 (1996).

Seipel, K. et al., "Different Activation Domains Stimulate Transcription from Remote ('enhancer') and Proximal ('promoter') Positions," *The EMBO Journal*, vol. 11, No. 13, 4961–8 (1992).

Silverman, N. et al., "Yeast ADA2 Protein Binds to the VP16 Protein Activation Domain and Activates Transcription," *PNAS*, vol. 91, 11665–8 (1994).

Spencer, D. et al., "Controlling Signal Transduction with Synthetic Ligands," *Science*, vol. 262, 1019–24 (1993).

Stade, K. et al., "Exportin 1 (Crm 1p) is a Essential Nuclear Export Factor," *Cell*, vol. 90, 1041–50 (1997).

Standaert, R. et al., "Molecular Cloning and Overexpression of the Human FK506–binding Protein FKBP," *Nature*, vol. 346, 671–4 (1990).

Steger, D. and Workman, J., "Remodeling Chromatin Structures for Transcription: What Happens to the Histones?" *BioEssays*, vol. 18, No. 11, 875–84 (1996).

Tjian, R. and Maniatis, T., "Transcriptional Activation: A Complex Puzzle with Few Easy Pieces," *Cell*, vol. 77, 5–8 (1994).

(List continued on next page.)

*Primary Examiner*—Robert A. Schwartzman
(74) *Attorney, Agent, or Firm*—Foley, Hoag & Eliot, LLP; Isabelle M. Clauss; Matthew P. Vincent

(57) ABSTRACT

Novel synthetic transcriptional modulators having at least one selected ligand linked to at least one transcriptional modulating portion are described. The transcriptional modulators of the present invention can include a ligand linked to a chemical moiety. These transcriptional modulators can be used to selectively control gene expression and to identify components of the transcriptional machinery.

35 Claims, 7 Drawing Sheets

OTHER PUBLICATIONS

Wermuth, J. et al., "Stereoisomerism and Biological Activity of the Selective and Superactive $\alpha_v\beta_3$ Integrin Inhibitor Cyclo(-RGDfV-) and its Retro–Inverso Peptide," *J. Am. Chem. Soc.*, vol. 119, No. 6, 1328–35 (1997).

Wolff, B. et al., "Leptomycin B is an Inhibitor of Nuclear Export: Inhibition of Nucleo–cytoplasmic Translocation of the Human Immunodeficiency Virus Type 1 (HIV–1) Rev Protein and Rev–dependent mRNA," *Chemistry and Biology*, vol. 4, 139–47 (1997).

* cited by examiner

SYNTHETIC TRANSCRIPTIONAL MODULATORS AND USES THEREOF

RELATED APPLICATIONS

This application is a continuation-in-part of U.S. patent application Ser. No. 08/987,912 filed on Dec. 9, 1997, the entire contents of which are hereby incorporated by reference (including the originally filed claims).

BACKGROUND OF THE INVENTION

Each of the roughly 100,000 genes encoded in the human genome is subject to individual dosage control. The systems that regulate gene expression respond to a wide variety of developmental and environmental stimuli, thus allowing each cell type to express a unique and characteristic subset of its genes, and to adjust the dosage of particular gene products as needed. The importance of dosage control is underscored by the fact that targeted disruption of key regulatory molecules in mice often results in drastic phenotypic abnormalities [Johnson, R. S., et al., Cell, 71:577–586 (1992)], just as inherited or acquired defects in the function of genetic regulatory mechanisms contribute broadly to human disease.

The regulatory mechanisms controlling the transcription of protein- coding genes by RNA polymerase II have been extensively studied. RNA polymerase II and its host of associated proteins are recruited to the core promoter through non-covalent contacts with sequence-specific DNA binding proteins [Tjian, R. and Maniatis, T., Cell, 77:5–8 (1994); Stringer, K. F., Nature (London), 345:783–786 (1990)]. An especially prevalent and important subset of such proteins, known as transactivators, typically bind DNA at sites outside the core promoter and activate transcription through space contacts with components of the transcriptional machinery, including chromatin remodeling proteins [Tjian, R. and Maniatis, T., Cell, 77:5–8 (1994); Stringer, K. F., Nature (London), 345:783–786 (1990); Bannister, A. J. and Kouzarides, T., Nature, 384:641–643 (1996); Mizzen, C. A., et al., Cell, 87:1261–1270 (1996)]. The DNA-binding and activation functions of transactivators generally reside on separate domains whose operation is portable to heterologous fusion proteins [Sadowski, I., et al., Nature, 335:563–564 (1988)]. Though it is believed that activation domains are physically associated with a DNA-binding domain to attain proper function, the linkage between the two need not be covalent [Belshaw, P. J., et al., Proc. Natl. Acad. Sci. USA, 93:4604–4607 (1996); Ho, S. H., et al., Nature (London), 382:822–826 (1996)]. In many instances, the activation domain does not appear to contact the transcriptional machinery directly, but rather through the intermediacy of adapter proteins known as coactivators [Silverman, N., et al., Proc. Natl. Acad. Sci. USA, 91:11005–11008 ((1994); Arany, Z., et al., Nature (London), 374:81–84 (1995)].

The importance of controlled gene expression in human disease and the information available to date relating to the mechanisms of gene regulation have fueled efforts aimed at discovering means of overriding endogenous regulatory controls or of creating new signaling circuitry in cells [Belshaw, P. J., et al., Proc. Natl. Acad. Sci. USA, 93:4604–4607 (1996); Ho, S. H., et al., Nature (London), 382:822–826 (1996); Rivera, V. M., et al., Nat. Med., 2:1028–1032; Spencer, D. M., et al., Science, 262:1019–1024 (1993)]. Of particular interest in this regard are small, membrane-permeant molecules designed to modulate gene transcription in living cells [Belshaw, P. J., et al., Proc. Natl. Acad. Sci. USA, 93:4604–4607 (1996); Ho, S. H., et al., Nature (London), 382:822–826 (1996); Rivera, V. M., et al., Nat. Med., 2:1028–1032; Spencer, D. M., et al., Science, 262:1019–1024 (1993)]. All such efforts involved genetic engineering of transcriptional modulatory protein domains such as naturally-occurring VP16. The present invention takes a significant departure from such art by relying upon chemical rather than biological means to harness the transcriptional machinery.

SUMMARY OF THE INVENTION

The present invention is based, at least in part, on the remarkable discovery that small molecular weight (e.g., <5kD), membrane-permeant compounds are capable of acting as transcriptional modulators. In preferred embodiments, the compounds of the invention, also referred to herein as transcriptional modulators, include at least one selected ligand linked, e.g., covalently linked, to at least one transcriptional modulating portion (TMP). The TMPs of the present invention can be chemical moieties, e.g., non-peptidyl, small molecules.

Accordingly, in one aspect, this invention pertains to methods and compositions for identifying novel transcriptional modulators. The method can be performed in a cell, e.g. cell-based, or in a reaction mixture, e.g., cell-free. In a cell based method, a cell is provided which has (a) a genetic construct encoding a chimeric protein and (b) a target gene under the control of at least one transcriptional regulatory element which is recognized by the DNA-binding domain of the chimeric protein. The chimeric protein includes at least one ligand-binding domain (which binds to a selected ligand) and a heterologous DNA-binding domain. The cell is contacted with a test compound under conditions which allow transcription to occur and any changes in transcriptional activity of the target gene in the presence of the test compound relative to that detected in the absence of the test compound are detected. A change in the level of transcription activity, e.g., an increase or decrease, of the target gene detected in the presence of the test compound relative to that detected in the absence of the test compound indicates that the test compound is a transcriptional modulator.

In preferred embodiments, the test compound(s) include a selected ligand linked to a test-transcriptional modulating portion (test-TMP). The identified transcriptional modulator (s) include a selected ligand linked to a TMP.

The present invention further provides a cell-free method for identifying a transcriptional modulator. The method involves providing a reaction mixture including a chimeric protein and a target gene under the control of at least one transcriptional regulatory element which is recognized by the DNA-binding domain of the chimeric protein. The reaction mixture further includes a cell-free transcription system and a test compound. Preferably, the cell-free transcription system is selected from a group consisting of a cell lysate, e.g., a HeLa cell extract, or a reconstituted protein mixture, e.g., a mixture of components of the transcriptional apparatus. The reaction mixture is provided under conditions which allow transcription to occur and any changes in transcriptional activity of the target gene in the presence of the test compound relative to that observed in the absence of the test compound are detected. In this assay, a change, e.g., an increase or a decrease, in the level of transcriptional activity of the target gene detected in the presence of the test compound relative to that detected in the absence of the test compound indicates that the test compound is a transcriptional modulator.

In yet another aspect, the invention features a method for identifying a transcriptional modulator from a plurality of test compounds. The method includes: providing cells, e.g., genetically engineered cells, which contain (i) a genetic construct encoding a chimeric protein which comprises at least one ligand-binding domain and a DNA-binding domain which is heterologous thereto, wherein the ligand-binding domain binds to a selected ligand; (ii) a target gene under the expression control of at least one transcriptional regulatory element which is recognized by the DNA-binding domain of the chimeric protein. These cells are contacted with one or more test compounds, each of which contain the selected ligand linked to at least one of a plurality of test-TMPs; and changes in transcription activity in the presence of the test compound are detected relative to that detected in the absence of the test compound. In this assay, a change, e.g., an increase or a decrease, in the level of transcriptional activity of the target gene detected in the presence of the test compound relative to that detected in the absence of the test compound indicates that the test compound is a transcriptional modulator.

Another aspect of the invention pertains to a method of modulating gene expression in a cell, e.g., a genetically-engineered cell. The method includes contacting the cell with a transcriptional modulator of the invention, such that modulation of gene expression occurs. In preferred embodiments, the cell, e.g., the genetically-engineered cell, contains a nucleic acid encoding a chimeric protein which comprises at least one ligand-binding domain and a DNA-binding domain heterologous thereto, and which binds to the transcriptional modulator. The cell can further include a target gene under the control of at least one transcriptional regulatory element which is recognized by the DNA-binding domain of the chimeric protein. In certain embodiments, the subject methods result in activation of transcription of the target gene. Alternatively, the subject methods result in inhibition of expression of a target gene, e.g., a constitutively active target gene.

In preferred embodiments, the transcriptional modulator is a membrane-permeant compound which binds to the chimeric protein and activates transcription of the target gene.

The subject method can be used on cells in culture, e.g. in vitro or ex vivo. For example, cells can be cultured in vitro in culture medium and the contacting step can be effected by adding the transcriptional modulator to the culture medium. Alternatively, the method can be performed on cells present in a subject, e.g., as part of an in vivo therapeutic protocol. For in vivo methods, the cells are within a subject and the contacting is effected by administering the transcriptional modulator to the subject. The activity of the transcriptional modulators of the invention can be further modulated by using a ligand which is not linked to a transcriptional modulating domain, which antagonizes the activity of the transcriptional modulator.

In yet another aspect, this invention pertains to a transcriptional modulator. The transcriptional modulator includes (i) at least one selected ligand which binds to a ligand-binding domain of a chimeric protein, linked directly or indirectly to (ii) a transcriptional modulating portion (TMP). The TMP is a portion which modulates transcription and includes one or more chemical moieties and/or one or more proteinaceous domains.

In preferred embodiments, the transcriptional modulator is a small molecule, e.g., a molecule having a molecular weight less than 5 kD, preferably less than 3 kD, and even more preferably, less than 1.5 kD. Preferably, the transcriptional modulator is membrane-permeant, e.g., it is capable of passing through a cell membrane.

In preferred embodiments, the transcriptional modulator is not itself the product of gene transcription or translation, e.g., it is not a protein.

In preferred embodiments, the selected ligand is linked to a TMP forming the transcriptional modulator. Preferably, the ligand is linked to the TMP through a covalent linkage, e.g., a covalent bond, a chiral linker or an achiral linker.

In preferred embodiments, the chimeric proteins of the invention include a ligand-binding domain which is capable of binding to at least one selected ligand molecule and a DNA-binding domain which is capable of binding to a particular DNA sequence(s). The ligand-binding protein is capable of binding with high affinity to at least one selected ligand molecule.

Other features and advantages of the invention will be apparent from the following detailed description, and from the claims.

DESCRIPTION OF THE DRAWINGS

FIG. 1A is a schematic representation of the synthesis of two transcriptional activators which consist of a modified FK506 derivative covalently linked to a 29-amino acid peptide of the Herpes Simplex Virus VP 16 activator domain (SEQ ID NO:1). The amino acids in the VP16 peptide can be either in the natural L stereochemical configuration (L-1), or in the nonnatural mirror-image D configuration D stereochemistry (D-1). Abbreviations: TBS, tert-butyldimethylsilyl, Boc, t-butyloxycarbonyl. BrAc$_2$O, bromoacetic acid anhydride; DMF, dimethylformamide; Me, Methyl.

FIG. 1B is a schematic representation of the structural relationship between L-1 and D-1 transcriptional activators. Both artificial activators, L-l and D-1, contain an identical FK506 moiety (tubular structure) attached through an achiral linker (wavy line) to either of two enantiomeric 29-mer activator peptides (twisted arrow).

FIG. 1C is a schematic representation of the synthetic activator serving as an intermediate between the DNA binding protein, GAL4-FKBP, and the basal transcriptional apparatus.

DETAILED DESCRIPTION OF THE INVENTION

Figure 1A:
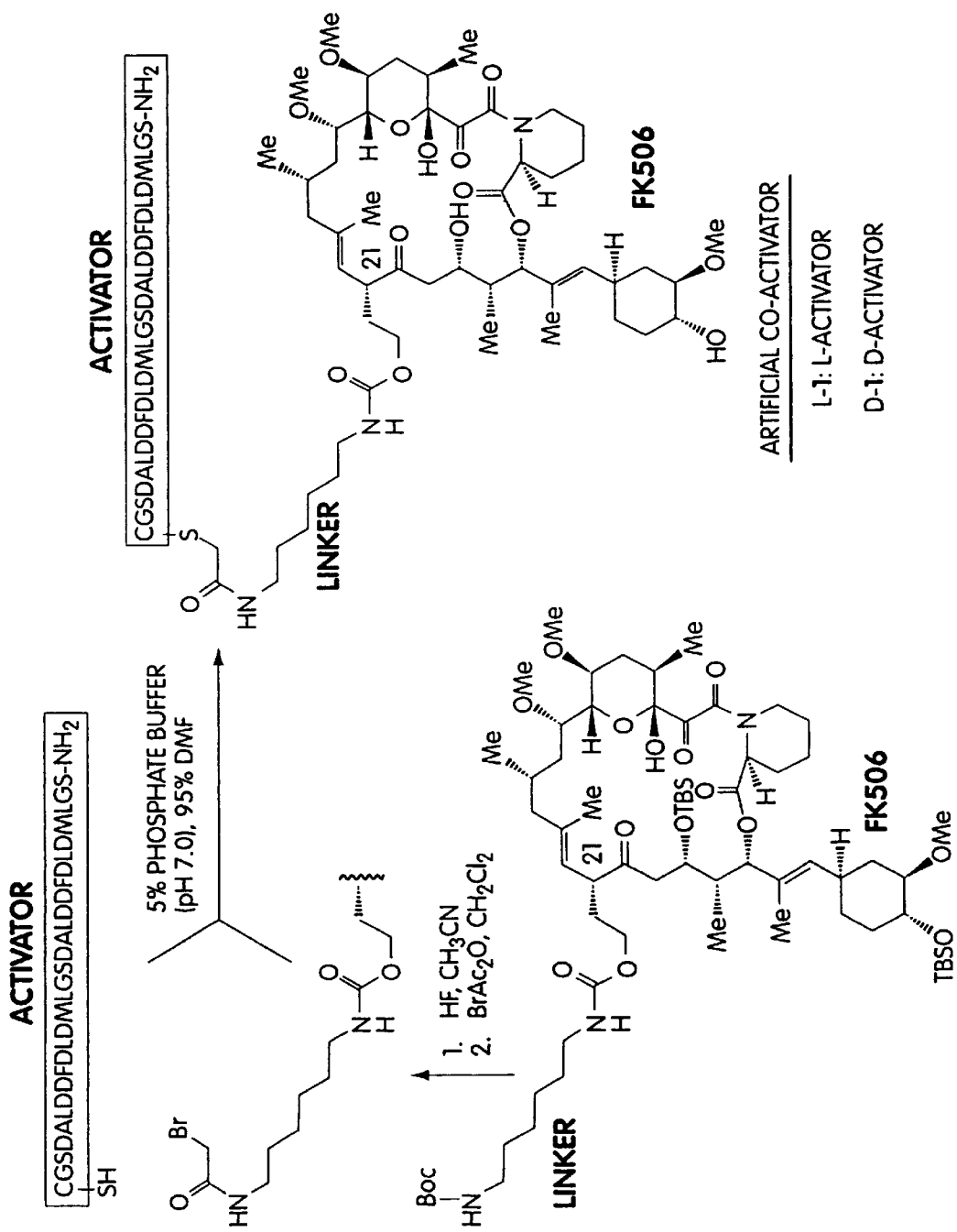
FIGS. 1A–1C are schematic representations of the synthesis and mechanism of activation of the transcriptional modulators (L-1 and D-1 transcriptional activators).

The present invention pertains, at least in part, to the discovery of small molecular weight (e.g., <5 kD), membrane-permeant non-proteinaceous compounds which are capable of modulating transcription, as well as methods of using the same to regulate gene expression, or to identify components of the transcriptional machinery. These transcriptional modulators include at least one selected ligand linked, e.g., covalently linked, directly or indirectly to at least one transcriptional modulating portion (TMP). The transcriptional modulators of the invention are capable of modulating transcription upon interaction with a chimeric protein containing at least one ligand-binding domain which recognizes the selected ligand fused directly or indirectly to at least one DNA-binding domain.

I. Methods for Identifying Novel Transcriptional Modulators

In one embodiment, the invention pertains to a method for identifying a transcriptional modulator. The method can be performed in a cell, e.g. cell-based or in a reaction mixture, e.g., cell-free. In a cell based method, a cell is provided which has a genetic construct encoding a chimeric protein and a target gene under the control of at least one transcriptional regulatory element which is recognized by the DNA-binding domain of the chimeric protein. The chimeric protein includes at least one ligand-binding domain which binds to a selected ligand and a DNA-binding domain which is heterologous thereto. The cell is further contacted with a test compound under conditions which allow transcription to occur and any changes in transcriptional activity of the target gene in the presence of the test compound relative to that detected in the absence of the test compound are detected. A change in the level of transcription activity of the target gene detected in the presence of the test compound relative to that detected in the absence of the test compound indicates that the test compound is a transcriptional modulator. The test compound(s) include a selected ligand for the chimeric protein linked to a test-transcriptional modulating portion (hereinafter test-TMP). The identified transcriptional modulator(s) include a selected ligand linked to a TMP. The test compounds and transcriptional modulators of the present invention are described in further detail below.

The present invention further provides a cell-free method for identifying a transcriptional modulator. The method involves providing a reaction mixture including a chimeric protein and a target gene under the control of at least one transcriptional regulatory element which is recognized by the DNA-binding domain of the chimeric protein. The reaction mixture further includes a cell-free transcription system and a test compound. Preferably, the cell-free transcription system is selected from a group consisting of a cell lysate, e.g., a HeLa cell extract, or a reconstituted protein mixture, e.g., a mixture of components of the trasncriptional apparatus. The reaction mixture is provided under conditions which allow transcription to occur and any changes in transcriptional activity of the target gene in the presence of the test compound relative to that detected in the absence of the test compound are detected. A change in the level of transcriptional activity of the target gene detected in the presence of the test compound relative to that detected in the absence of the test compound indicates that the test compound is a transcriptional modulator.

Changes in transcriptional activity can be detected by variations in the expression of a target gene (e.g., a reporter gene), e.g., variations in the observed levels of mRNA, or protein product encoded by the target gene. As used in the methods described herein, by "target gene" is meant a gene whose expression may be assayed; such genes include, without limitation, genes conferring a drug resistant phenotype (e.g., resistance to chloroamphenicol or neomycin), genes whose expression products provide for colorimetric, fluorescent or luminescent detection (e.g., Green Fluorescent Protein (GFP), SEAP, β-galactosidase or luciferase), a gene whose expression product rescues an auxotrophic phenotype (e.g., LEU2, HIS3, URA3 or LYS2), or a gene encoding any cell surface antigen for which antibodies are available (e.g., for panning).

Test Compound

The test compound can be designed to incorporate a moiety known to bind to a component of the transcription machinery or to have transcriptional modulating activity, or can be selected from a library of diverse compounds, e.g., based on a desired activity, e.g., random drug screening based on a desired activity. Preferably, the test compound of the present invention is a small molecule having a chemical moiety, e.g., a non-peptidyl moiety as the TMP. The terms "chemical moiety" or "moiety" are intended to include synthetic and naturally-occurring non-proteinaceous entities. For example, chemical moieties include unsubstituted or substituted alkyl, aromatic, or heterocyclyl moieties including macrolides, leptomycins and related natural products or analogs thereof. The particular components of the test compound are discussed in detail below in the Transcriptional Modulator and/or Test Compound section.

Libraries of Test Compounds

Novel transcriptional modulators can be identified by linking, e.g., covalently linking, e.g., a test library to a selected ligand such that the test library is targeted to the transcriptional machinery. Exemplary test libraries that can be used include combinatorial libraries.

In one embodiment, the invention provides libraries of transcriptional modulators. The synthesis of combinatorial libraries is well known in the art and has been reviewed (see, e.g., E. M. Gordon et al., J. Med. Chem. (1994) 37:1385–1401 DeWitt, S. H.; Czarnik, A. W. Acc. Chem. Res. (1996) 29:114; Armstrong, R. W.; Combs, A. P.; Tempest, P. A.; Brown, S. D.; Keating, T. A. Acc. Chem. Res. (1996) 29:123; Ellman, J. A. Acc. Chem. Res. (1996) 29:132; Gordon, E. M.; Gallop, M. A.; Patel, D. V. Acc. Chem. Res. (1996) 29:144; Lowe, G. Chem. Soc. Rev. (1995) 309, Blondelle et al. Trends Anal. Chem. (1995) 14:83; Chen et al. J. Am. Chem. Soc. (1994) 116:2661; U.S. Pat. Nos. 5,359,115, 5,362,899, and 5,288,514; PCT Publication Nos. WO92/10092, WO93/09668, WO91/07087, WO93/20242, WO94/08051). The subject invention includes methods for synthesis of combinatorial libraries of transcriptional modulators. Such libraries can be synthesized according to a variety of methods. In one illustrative method, a selected ligand portion is chemically linked (covalently or non-covalently) to a transcriptional modulating portion (TMP), optionally by means of a linker portion. Thus, in certain embodiments, a compound of the invention can be represented by the formula A-B-C, in which A is a selected ligand (e.g., as described hereinbelow under the heading "Selected Ligands"); B is a direct (preferably single) bond or a linker portion; and C is a TMP. Exemplary transcriptional modulating portions are described hereinbelow (e.g., under the heading "Transcriptional Modulating Portions (TMP)", and include portions which are capable of interacting directly or indirectly with the transcriptional machinery of a cell, or otherwise modulates transcriptional activity, e.g., by modulating (i.e., increase or decrease) the nuclear transport (e.g., import or export) of a transcriptional modulator, thereby modulating the effective concentration of the transcriptional modulator in the cell nucleus.

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allow to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the TMP are selected non-randomly, e.g., to provide a TMP having known structural similarity or homology to a known modulator of transcription. It will be appreciated that a wide variety of peptidic, peptidomimetic, or non-peptidic compounds can be readily generated in this way.

The "split-pool" strategy results in a library of peptides, e.g., TMPs, which can then be linked, covalently or non-covalently, to a selected ligand (e.g., as described herein), thereby preparing a library of test compounds of the invention. In one embodiment, an amino acid residue (e.g., a terminal amino acid residue) of a peptidic TMP can be a cysteine residue; the side-chain thiol group of the cysteine can be used for attachment of the peptide to a ligand (e.g., FK506 or an analog or derivative thereof). Thus, attachment of the FK506 derivative to the combinatorial peptide library provides a library of hybrid ligand-peptide compounds which can then be screened for transcriptional modulating activity as described herein.

In another illustrative synthesis, a "diversomer library" is created by the method of Hobbs DeWitt et al. (*Proc. Natl. Acad. Sci U.S.A.* 90:6909 (1993)). Other synthesis methods, including the "tea-bag" technique of Houghten (see, e.g., Houghten et al., *Nature* 354:84–86 (1991)) can also be used to synthesize libraries of compounds according to the subject invention.

In certain embodiments, the invention relates to libraries of compounds which can modulate transcription by modulating import or export of transcriptional modulating compounds into or out of the cell nucleus. In this embodiment, the TMP can be, e.g., a portion which regulates or modulates nuclear import or export. A compound of the invention having a selected ligand portion and nuclear exporting portion can bind to a fusion protein having a ligand-binding domain and promote the export of the fusion protein from the nucleus. (For a general discussion of nuclear protein import, see, e.g., Gorlich, D. *Curr. Opin. Cell. Biol.* (1997) 9:412–419). Thus, the effective nuclear concentration of a fusion protein having a DNA-binding domain, a ligand-binding domain and a transcriptional modulating domain can be modulated by a hybrid compound of the invention, thereby modulating transcriptional modulating activity. One example of a modulator of nuclear export is leptomycin B. Thus, a library of compounds in which the TMP is a library of leptomycin analogs or derivatives, can be prepared. Leptomycin B has a carboxylate group which can be conveniently coupled to a ligand portion to provide a hybrid compound of the invention.

Libraries of compounds can be screened to determine whether any members of the library have a desired activity, and, if so, to identify the active species. Methods of screening combinatorial libraries have been described (see, e.g., Gordon et al., *J. Med. Chem.,* supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, minescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention which include a ligand portion and a transcriptional modulating portion which is capable of interacting with the transcriptional machinery of a cell can be screened for transcriptional modulating activity by assaying the activity of each compound, e.g., by incubating the test compound with a cell or nuclear extract, e.g., in one well of a multiwell plate, such as a standard 96-well microtiter plate. In this embodiment, the activity of each individual compound can be determined. Thus, for example, a plurality of test compounds can be screened by incubation of each compound in a well of a multiwell plate containing a HeLa nuclear extract (e.g., prepared as described infra) and a chimeric or fusion protein which includes a ligand binding domain, to which the ligand portion of the test compound can bind. A well or wells having no test compound can be used as a control. After incubation, the activity of each test compound can be determined by assaying each well for a product of gene transcription. Thus, the activities of a plurality of test compounds can be determined in parallel.

In another embodiment of a screening assay, a compound (or compounds) of the invention can be screened by contacting the compound with an engineered cell in vitro. For example, as described infra, a Jurkat cell transfected with a reporter gene, e.g., a secreted alkaline phosphatase (SEAP) gene under the expression control of a suitable promoter (see, e.g., PCT Application No. PCT/US94/01617) together with a DNA construct encoding a chimeric protein of this invention can be incubated with a test compound. The fusion protein can include a DNA-binding domain, and a ligand binding domain, to which the ligand portion of the test compound can bind, as described herein. A test compound with transcriptional activating activity will bind to the ligand-binding domain of the fusion protein and increase transcription of the AP gene and secretion of AP by the cell; the AP secretion readily can be detected by known methods. Thus, the test compounds of the invention can be rapidly screened for transcriptional activating activity. Other reporter genes (such as luciferase or beta-galactosidase) can be used to detect transcriptional activating activity, as the ordinarily skilled artisan will appreciate.

Another embodiment relies upon the use of an auxotrophic yeast strain engineered to contain a gene which complements the auxotrophy under the control of a transcription regulatory element which is recognized by the DNA-binding domain of a chimeric protein.

Another embodiment relies upon a cell (e.g., a yeast cell) lacking a gene required for biosynthesis of an essential nutrient (such as, e.g., the amino acid histidine) can be grown in a medium in which the nutrient is lacking, in the presence of a plasmid containing the gene (e.g., HIS, a histidine synthesis construct) under the control of an appropriate control sequence. In the absence of a transcriptional activator, little or no cell growth will be seen. However, in the presence of a compound which has transcriptional activating activity, the cell can express the required gene product; accordingly, cell growth can be observed when an active compound is present.

In still another embodiment, large numbers of test compounds can be simultaneously tested for transcriptional modulating activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads.

The effect of the test compound on the cell (e.g., cell growth, cell death, production of gene products, and the like) can then be measured to determine the effect of the test compound on translation. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of transcriptional modulator compounds of the invention contain at least 30 compounds, more preferably at least 100 compounds, and still more preferably at least 500 compounds. In preferred embodiments, the libraries of transcriptional modulator compounds of the invention contain fewer than $10^9$ compounds, more preferably fewer than $10^8$ compounds, and still more preferably fewer than $10^7$ compounds.

II. Methods of Modulating Gene Expression

Another aspect of the invention pertains to a method of modulating gene expression in a cell. The method includes contacting the cell with a transcriptional modulator of the invention, such that modulation of gene expression occurs. Preferably, the cell contains a genetic construct encoding a chimeric protein which includes at least one ligand-binding domain which binds to the ligand of the transcriptional modulator, fused to a heterologous DNA-binding domain. In certain embodiments, e.g., those involving regulated nuclear import or export, the chimeric protein can additionally include a transcriptional modulating domain. Generally, the cell can further include a target gene under the control of at least one transcriptional regulatory element which is recognized by the DNA-binding domain of the chimeric protein. The subject method can lead to activation of transcription of the target gene, or to inhibition of expression of a target gene, e.g., a constitutively active target gene.

"Cells," "genetically-engineered cells" or "recombinant cells" are art recognized terms and the decription below applies to these cells interchangeably. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The subject method can be used on cells in culture, e.g. in vitro or ex vivo, as shown in the Examples herein. For example, cells can be cultured in vitro in culture medium and the contacting step can be effected by adding the transcriptional modulator to the culture medium. Alternatively, the method can be performed on cells present in a subject, e.g., as part of an in vivo therapeutic protocol. For in vivo methods, the cell is preferably found in a subject and the contacting is effected by administering the transcriptional modulator to the subject. As used herein, the language "subject" is intended to include human and non-human animals. The term "non-human animals" includes all vertebrates, e.g., mammals and non-mammnals, such as non-human primates, sheep, dog, cow, chickens, amphibians, reptiles, etc. In certain embodiments, the subject is a mammal, e.g., a primate, e.g., a human.

The cells used in the methods described herein may be procaryotic, but are preferably eucaryotic, including plant, yeast, worm, insect and mammalian. At present it is especially preferred that the cells be mammalian cells, particularly primate, more particularly human, but can be associated with any animal of interest, particularly domesticated animals, such as equine, bovine, murine, ovine, canine, feline, etc. Among these species, various types of cells can be involved, such as hematopoietic, neural, mesenchymal, cutaneous, mucosal, stromal, muscle, spleen, reticuloendothelial, epithelial, endothelial, hepatic, kidney, gastrointestinal, pulmonary, etc. Of particular interest are hematopoietic cells, which include any of the nucleated cells which may be involved with the lymphoid or myelomonocytic lineages. Of particular interest are members of the T- and B-cell lineages, macrophages and monocytes, myoblasts and fibroblasts. Also of particular interest are stem and progenitor cells, such as hematopoietic neural, stromal, muscle, hepatic, pulmonary, gastrointestinal, etc. Most preferably, the cells are muscle cells.

The cells can be autologous cells, syngeneic cells, allogenic cells and even in some cases, xenogeneic cells. The cells may be modified by changing the major histocompatibility complex ("MHC") profile, by inactivating $b_2$microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

The activity of the transcriptional modulators of the invention can be further modulated by using a free monomeric ligand, e.g., a ligand which is not linked to a TMP, which antagonizes the activity of the transcriptional modulator. These free ligands may competitively interact with a ligand-binding protein to decrease or eliminate its transcriptional modulatory activity. Thus, if one wishes to rapidly terminate the effect of cellular activation, a cell exposed to a transcriptional modulator of the invention can be contacted with the free ligand to reduce or eliminate the transcriptional activity of the modulator.

Target Genes

As used herein, the term "target gene" refers to a gene which includes a transcriptional initiation region having a target DNA sequence(s) or responsive element which is recognized by the DNA-binding domain of a chimeric protein, so as to be responsive to signal initiation from the TMP. In certain embodiments, signal initiation leads to transcription activation and expression of one or more target genes. Alternatively, signal initiation can lead to inhibition of transcription of an active target gene, e.g., a constitutively active target gene. The target genes may be an endogenous or exogenous gene. By "exogenous gene" is meant a gene which is not otherwise normally expressed by the cell, e.g. because of the nature of the cell, because of a genetic defect of the cell, because the gene is from a different species or is a mutated or synthetic gene, or the like. Such gene can encode a protein, antisense molecule, ribozyme etc., or can be a DNA sequence comprising an expression control sequence linked or to be linked to an endogenous gene with which the expression control sequence is not normally associated. Conversely, an "endogenous gene" refers to a gene which is normally expressed in a given cell.

Accordingly, the constructs containing the target genes can have a "transcriptional regulatory sequence". This term refers to one or more responsive element(s) in the 5' region which is operably linked to a target gene. By "operably linked" is meant that a gene and a regulatory sequence(s) are connected in such a way as to permit gene expression when the appropriate molecules (e.g., chimeric proteins bound to synthetic transcriptional modulator or a target gene) are bound to the regulatory sequences. The responsive elements (s) is recognized by the DNA-binding domain of the chimeric receptor protein and responds to the interaction between the transcriptional modulator and the chimeric protein. In preferred embodiments, transcription of a target gene is under the control of a promoter sequence (or other transcriptional regulatory sequence) which controls the expression of the recombinant gene in a cell-type in which expression is intended. It will be understood that the recombinant gene can be under the control of transcriptional regulatory sequences which are the same or which are different from those sequences which control transcription of the naturally-occurring form of the target gene.

The expression construct will therefore have at its 5' end in the direction of transcription, the responsive element and the promoter sequence which allows for induced transcription initiation of a target gene of interest, usually a therapeutic gene. The transcriptional termination region is not as important, and can be used to enhance the lifetime of or make short half-lived mRNA by inserting AU sequences which serve to reduce the stability of the mRNA and, therefore, limit the period of action of the protein. Any region can be employed which provides for the necessary transcriptional termination, and as appropriate, translational termination.

The responsive element can be a single recognition sequence or multiple recognition sequences.

Homologous recombination can also be used to replace endogenous transcriptional control sequences with a transcriptional control element which is recognized by a chimeric protein of this invention.

A wide variety of genes can be employed as the target gene, including genes that encode a protein of interest or an antisense sequence of interest or a ribozyme of interest. The target gene can be any sequence of interest which provides a desired phenotype. The target gene can express a surface membrane protein, a secreted protein, a cytoplasmic protein, or there can be a plurality of target genes which can express different types of products. The target gene may be an antisense sequence which can modulate a particular pathway by inhibiting a transcriptional regulation protein or turn on a particular pathway by inhibiting the translation of an inhibitor of the pathway. The target gene can encode a ribozyme which may modulate a particular pathway by interfering, at the RNA level, with the expression of a relevant transcriptional modulator or with the expression of an inhibitor of a particular pathway. The proteins which are expressed, singly or in combination, can involve homing, cytotoxicity, proliferation, immune response, inflammatory response, clotting or dissolving of clots, hormonal regulation, or the like. The proteins expressed could be naturally-occurring, mutants of naturally-occuring proteins, unique sequences, or combinations thereof. Particularly preferred examples of target genes encode a protein selected from a growth or a differentiation factor, a protein involved in clotting or thrombolyis, a protein involved in promoting or inhibiting vascularization, a protein involved in metabolic regulation, an enzyme, or a tumor suppressor.

The target gene can be any gene which is secreted by a cell, so that the encoded product can be made available at will, whenever desired or needed by the host. Various secreted products include hormones, such as endostatin, angiostatin, insulin, human growth hormone, glucagon, pituitary releasing factor, ACTH, melanotropin, relaxin, etc.; differentiation or growth factors, such as EGF, IGF-1, TGF-α, -β, PDGF, G-CSF, M-CSF, GM-CSF, FGF, erythropoietin, neurotrophins, e.g., nerve growth factor (NGF), brain-derived neurotrophic facto (BDNF), neurotrophin-3 (NT-3), megakaryocytic stimulating and growth factors, etc.; interleukins, such as IL-1 to -13; TNF-α and -β, etc.; soluble receptors for TNF or IL-1, or receptor antagonists therefor; enzymes, such as tissue plasminogen activator, members of the complement cascade, perforins, superoxide dismutase, coagulation factors, antithrombin-III, Factor VIIc, Factor VIIIvW, a-anti-trvpsin, protein C, protein S, endorphins, dynorphin, bone morphogenetic protein, CFTR, etc.; and leptin and leptin receptor molecules.

The target gene can be any gene which is naturally a surface membrane protein or made so by introducing an appropriate signal peptide and transmembrane sequence. Various proteins include homing receptors, e.g. L-selectin (Mel-14), blood-related proteins, particularly having a kringle structure, e.g. Factor VIIIc, Factor VIIIvW, hematopoietic cell markers, e.g CD3, CD4, CD8, B cell receptor, TCR subunits α, β, γ, δ, CD10, CD19, CD28, CD33, CD38, CD41, etc., receptors, such as the interleukin receptors IL-2R, IL-4R, etc., channel proteins, for influx or efflux of ions, e.g. $H^+$, $Ca^{+2}$, $K^+$, $Na^+$, $Cl^-$, etc., and the like; CFTR, tyrosine activation motif, z activation protein, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric proteins for exocytosis allows for rapid transfer of the proteins to the extracellular medium and a relatively high localized concentration.

Also, intracellular proteins can be of interest, such as proteins in metabolic pathways, modulatory proteins, steroid receptors, transcription factors, etc., particularly depending upon the nature of the host cell. Some of the proteins indicated above can also serve as intracellular proteins.

The following are a few illustrations of different target genes. In T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cells keratinocytes, one could provide for infectious protection, by secreting α-, β- or -γ interferon, antichemotactic factors, proteases specific for bacterial cell wall proteins, etc.

In addition to providing for expression of a target gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-selectin, GMP140, CLAM-1, etc., or addressing, e.g ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

In many situations one may wish to be able to kill the modified cells, where one wishes to terminate the treatment, the cells become neoplastic, in research where the absence of the cells after their presence is of interest, or other event. For this purpose one can provide for the expression of the Fas antigen or TNF receptor fused to a binding moiety. (Watanable-Fukunaga et al. *Nature* (1992) 356, 314–317) In the original modification, one can provide for constitutive expression of such constructs, so that the modified cells have such proteins on their surface or present in their cytoplasm. Alternatively, one can provide for controlled expression, where the same or different ligand can initiate expression and initiate apoptosis. By providing for the cytoplasmic portions of the Fas antigen or TNF receptor in the cytoplasm joined to binding regions different from the binding regions associated with expression of a target gene of interest, one can kill the modified cells under controlled conditions.

III. Transcriptional Modulators and/or Test Compounds

The present invention further pertains to transcriptional modulators. The transcriptional modulator has (i) at least one selected ligand which binds to a ligand-binding domain of a chimeric protein linked to (ii) a transcriptional modulating portion (TMP) forming the transcriptional modulator. The transcriptional modulator can be a "small molecule" in that it includes a molecule having a molecular weight of less than about 5 kD. The transcriptional regulator can be membrane permeant, e.g., capable of passing through a cell membrane.

The present invention also includes combinations of transcriptional odulators. The combinations of transcriptional modulators can be used in the methods described herein. The transcriptional modulators used in the combinations can affect the activity of each other. For example, the combination of transcriptional modulators can act synergistically, additively, or even in some instances counteract each other to some extent. The present invention also includes membrane-permeant formulations. In membrane-permeant formulations, at least one transcriptional modulator is combined with an agent which enhances membrane permeability of the transcriptional modulator, Examples of such agents include a detergent, such as digitonin.

It should be understood that the test compound(s) described above are being screened for the ability to serve as transcriptional modulators of the present invention. In the context of the present invention, the test compound is a selected ligand linked to a test-TMP which is a TMP being tested for its ability to modulate transcription. The definitions set forth below with respect to the selected ligand and/or TMP also apply to the test compound.

The transcriptional modulator can have the following formula:

$$(Ligand)_n-Linker-(TMP)_n$$

wherein n is an integer from 1 to about 4. A preferred transcriptional modulator has the formula: $(Ligand)_1-Linker-(TMP)_1$. In transcriptional modulators where n>than 1, either one of the ligand or the TMP may be the same or different molecules. Exemplary ligands and transcriptional modulators are described in detail below.

The language "small molecule" is intended to include a molecule which is not itself the product of gene transcription of translation, i.e., it is not a protein, RNA or DNA. Preferably, a "small molecule" has a molecular weight of less than 5 kD, preferably less than 3 kD, and even more preferably, less than 1.5 kD.

Preferred transcriptional modulators are membrane-permeant. As used herein, the term "membrane-permeant transcriptional modulators" is intended to include molecules which are capable of translocating across the membrane of a cell in a form that allows the molecule to perform its intended function. Accordingly, the size and the hydrophobicity of the membrane-permeant transcriptional modulators can be determined such that transfer across the cell membrane is effected. The cells may be procaryotic, but are preferably eucaryotic, and most preferably mammalian cells. The membrane can consist of primarily a double layer of lipid molecules and associated proteins that enclose all cells, and, in eucaryotic cells, many organelles. As described in detail herein, various ligands and TMPs are hydrophobic or can be made so by appropriate modification with lipophilic groups. Particularly, the covalent linkage bridging the ligand and transcriptional modulator moiety can serve to enhance the lipophilicity of the transcriptional modulators by providing aliphatic side chains of from about 12 to 24 carbon atoms. Alternatively, one or more groups can be provided which will enhance transport across the membrane, e.g., without endosome formation.

Applicable and readily observable or measurable criteria for selecting a transcriptional modulator include: (A) the transcriptional modulator is physiologically acceptable (i.e., lacks undue toxicity towards the cell or animal for which it is to be used), (B) the transcriptional modulator has a reasonable therapeutic dosage range, (C) desirably (for applications in whole animals, including gene therapy applications), it can be taken orally (is stable in the gastrointestinal system and absorbed into the vascular system), (D) it can cross the cellular and other membranes, as necessary.

Selected Ligands

The terms "selected ligand" or "ligand" are art-recognized and are intended to include a molecule that binds to a protein or other molecule, e.g., through a ligand-binding domain of said protein. A transcriptional modulator of the present invention comprises a ligand moiety which brings the TMP in close proximity to the target gene. Measurable criteria for selecting a ligand include a ligand which binds to a ligand-binding domain (also referred to herein as a receptor) with reasonable affinity for the desired application. A first desirable criterion is that the compound is relatively physiologically inert, but for its binding to the ligand-binding domain. The less the ligand binds to native proteins, the better the response will normally be. For the most part, the ligands can be non-peptide and non-nucleic acid.

There are a variety of naturally-occurring receptors for small non-proteinaceous organic molecules, which small organic molecules fulfill the above criteria. Substantial modifications of these compounds are permitted, so long as the binding capability is retained and with the desired specificity. Exemplary compounds include macrocyclic molecules, e.g., macrolides. Suitable binding affinities will be reflected in Kd values well below about $10^{-4}$ M, preferably below about $10^{-6}$ M, more preferably below about $10^{-7}$ M, even more preferably below about $10^{-8}$ M, and in some embodiments below about $10^{-9}$ M.

Preferred ligands are membrane permeant, i.e., ligands are selected such as to be able to translocate across the membrane. Various ligands are hydrophobic or can be made so by appropriate modification with lipophilic groups. Alternatively, one or more groups can be provided which will enhance transport across the membrane, desirably without endosome formation.

Examples of ligands include FK506, FK520, rapamycin, cyclosporin A, tetracycline, steroid, e.g, estrogen, ecdysone, or glucocorticoid, vitamin D, and derivatives thereof, which retain their binding capability to the natural or mutagenized ligand-binding domain. The present invention takes advantage of the high affinity interaction involving the ligand and its natural receptor(s), e.g., the interaction between FK506 and an immunophilin receptor, e,g, FKBP12; cyclosporin A and a cyclophilin receptor; a steroid and a steroid receptor, e.g., estrogen with an estrogen receptor, ecdysone with an ecdysone receptor, or glucocorticoid with a glucocorticoid receptor; tetracycline with the tetracycline receptor; vitamin D with the vitamin D receptor; rapamycin with FKBP which may fuirther associate with a large mammalian protein termed FRAP, and the like (See e.g., WO 96/41865).

Preferably, one uses a derivative of such a ligand which has substantially lower binding affinity for the ligand's native receptor as compared to binding to genetically engineered variants thereof which can be used in the chimeric proteins. As describe in detail below, in addition to modifying the ligand, it is desirable to change the binding protein to accommodate the change in the ligand. For example, one can prepare modified ligands that will fail to bind appreciably to their wildtype receptors (e.g., FKBP12) due to the presence of substituents ("bumps") on the reagents that sterically clash with sidechain residues in the receptor's binding pocket. One may also make corresponding receptors that contain mutations at the interfering residues ("compensatory mutations") and therefore gain the ability to bind ligands with bumps. Using "bumped" ligand moieties and receptor moieties bearing compensatory mutations enhances the specificity and thus the potency of our reagents. Bumped reagents should not bind to the endogenous, wildtype receptors, which can otherwise act as a "sink" toward transcriptional modulators based on natural ligand moieties.

In preferred transcriptional modulators, the biological activity of the ligand is reduced, most preferably lost, by virtue of the linkage to the transcriptional modulatory portion, or through bump/hole modifications described herein. For example, as described in the Examples below, derivatives of FK506 can be prepared to yield derivatives that lack immunosuppressive properties but retain the ability to bind FKBP with high affinity (Belshaw, P. J. et al. (1996) *Proc. Natl. Acad. Sci. USA* 93: 4604–4607; Bierer, B. E. et al. (1990) *Science* 250: 556–559). Similarly, ligands such as cyclosporin A (CsA), which is a cyclic undecapeptide that binds with high affinity (6 nM) to its intracellular receptor cyclophilin, an 18 kDa monomeric protein, can be modified to reduce or eliminate its immunosuppressive properties. Other ligands which can be used are steroids. By way of non-limiting example, glucocorticoids, ecdysone, and estrogens can be used.

Sites of interest for linking of FK506 and analogs thereof include positions involving annular carbon atoms from about 17 to 24 and substituent positions bound to those annular atoms, e.g. 21 (allyl), 22, 37, 38, 39 and 40, or 32 (cyclohexyl), while the same positions except for 21 are of interest for FK520. For cyclosporin, sites of interest include MeBmt, position 3 and position 8.

Examples of additional modifications include modifying the groups at position 9 or 10 of FK506 (see Van Duyne et al (1991) *Science* 252, 839), so as to increase their steric requirement, by replacing the hydroxyl with a group having greater steric requirements, or by modifing the carbonyl at position 10, replacing the carbonyl with a group having greater steric requirements or functionalizing the carbonyl, e.g. forming an N-substituted Schiffs base or imine, to enhance the bulk at that position.

Various functionalities which can be conveniently introduced at those sites are alkyl groups to form ethers, acylamido groups, N-alkylated amines, where a 2-hydroxyethylimine can also form a 1,3-oxazoline, or the like. Generally, the substituents will be from about 1 to 6, usually 1 to 4, and more usually 1 to 3 carbon atoms, with from 1 to 3, usually 1 to 2 heteroatoms, which will usually be oxygen, sulfur, nitrogen, or the like. By using different derivatives of the basic structure, one can create different ligands with different conformational requirements for binding. By mutagenizing receptors, one can have different receptors of substantially the same sequence having different affinities for modified ligands not differing significantly in structure.

"Bumped" monomeric and dimeric ligands have been prepared using C10 acetamide and formamide derivatives of FK506. Spencer et al, "Controlling Signal Transduction with Synthetic Ligands," *Science* 262 5136 (1993): 1019–1024. Preferred "bumped" modifications of derivatives of FK506 include one change at C10 and one at C9 of FK506. The R- and S-isomers of the C10 acetamide and formamide of FK506 have been synthesized by standard techniques. These bumped derivatives have lost at least three orders of magnitude in their binding affinity towards FKBP12. The affinities were determined by measuring the ability of the derivatives to inhibit FKBP12's rotamase activity.

An illustrative member of a second class of C9-bumped derivatives is the spiro-epoxide, which has been prepared by adaptation of known procedures. See e.g., Fisher et al, *J Org Chem* 56 8(1991): 2900–7 and Eidmunds et al, *Tet Lett* 32 48 (1991):819–820. A particularly interesting series of C9 derivatives are characterized by their sp3 hybridization and reduced oxidation state at C9.

Limand-Binding Domain

The language "ligand-binding domain" is intended to include a molecule, e.g., a protein, that binds to a selected ligand and initiates a response, e.g., a change in transcriptional activity. Preferably, the ligand-binding domain is fused to, e.g., covalently linked to, a heterologous moiety to form a chimeric protein. The ligand-binding domain can be any convenient moiety which will allow for induction using a natural or unnatural ligand, preferably an unnatural synthetic ligand. A wide variety of binding proteins, including receptors, are known, which can be used as ligand-binding as indicated above. Of particular interest are binding proteins for which ligands (preferably small organic ligands) are known or may be readily produced. These receptors or ligand binding moieties include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. For the most part, the receptor moieties will be at least about 50 amino acids, and fewer than about 350 amino acids, usually fewer than 200 amino acids, either as the natural moiety or truncated active portion thereof. Preferably the binding moiety will be small (<25 kDa, to allow efficient transfection in viral vectors), monomeric, nonimmunogenic, and should have synthetically accessible, cell permeant, nontoxic ligands, e.g., ligand-transcriptional modulating moieties, that can modulate transcription.

Preferred FKBPs are the cytosolic receptors for macrolides such as FK506, FK520 and rapamycin and are highly conserved across species. Information concerning the nucleotide sequences, cloning, and other aspects of various FKBP receptors is known in the art, which permitting the synthesis or cloning of DNA encoding the desired FKBP peptide sequence, e.g., using known methods and PCR primers based on published sequences. See e.g. Staendart et al, 1990, Nature 346, 671–674 (human FKBP12); Kay, 1996, Biochem. J. 314, 361–385 (review). Homologous FKBP proteins in other mammalian species, in yeast, and in other organsirns are also known in the art and may be used in the chimeric proteins disclosed herein. See e.g. Kay, 1996, *Biochem. J.* 314, 361–385 (review). The size of FKBP domains. for use in this invention varies, depending on which FKBP protein is employed. FKBP may additionally comprise a naturally-occurring peptide sequence derived from the human FKBP12 protein or a peptide sequence derived from another human FKBP, from a murine or other mammalian FKBP, or from some other animal, yeast or fungal FKBP. Preferred FKBPs may contain up to about ten (preferably 1–5) amino acid substitutions, insertions or deletions within that region relative to the naturally-occurring sequence; may be a peptide sequence encoded by a DNA sequence capable of selectively hybridizing to a DNA molecule encoding a naturally-occuring FKBP or may be encoded by a DNA sequence which would be capable, but for the degeneracy of the genetic code, of selectively hybridizing to a DNA molecule encoding a naturally-occurring FKBP.

"Capable of selectively hybridizing" as that phrase is used herein means hat two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6× SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

In certain embodiments, an FKBP peptide sequence for use in chimeric proteins will be capable of participating in a dimer, trimer or multimer, for example, in a complex with a another protein such as FRB-containing protein (as may be determined by any means, direct or indirect, for detecting such binding). "Dimerization", "oligomerization" and "multimerization" refer to the association of two or more proteins, mediated, in the practice of this invention, by the binding of each such protein to a common ligand; Detailed construction of FKBP, FRB- containing chimeras are described in WO96/41865.

The portion of the construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding. Detailed protocols for generating such mutations are provided in WO96/41865. Illustrative of this situation is to modify FKBP12's Phe36 to Ala and/or Asp37 to Gly or Ala to accommodate a substituent at positions 9 or 10 of FK506 or FK520. In particular, mutant FKBP12 moieties which contain Val, Ala, Gly, Met or other small amino acids in place of one or more of Tyr26, Phe36, Asp37, Tyr82 and Phe99 are of particular interest as receptor moieties for FK506-type and FK-520-type ligands containing modifications at C9 and/or C10.

The ability to employ in vitro mutagenesis or combinatorial modifications of sequences encoding proteins allows for the production of libraries of proteins which can be screened for binding affinity for different ligands. For example, one can totally randomize a sequence of 1 to 5, 10 or more codons, at one or more sites in a DNA sequence encoding a binding protein, make an expression construct and introduce the expression construct into a unicellular microorganism, and develop a library. One can then screen the library for binding affinity to one or desirably a plurality of ligands. The best affinity sequences which are compatible with the cells into which they would be introduced can then be used as the binding domain. The ligand would be screened with the host cells to be used to determine the level of binding of the ligand to endogenous proteins. A binding profile could be defined weighting the ratio of binding affinity to the mutagenized binding domain with the binding affinity to endogenous proteins. Those ligands which have the best binding profile could then be used as the ligand. Phage display techniques, as a non-limiting example, can be used in carrying out the foregoing.

Single or multiple mutants of a ligand-binding domain can be generated by co-randomizing structurally-identified residues that are or would be in contact with or near one or more ligand substituents. For example, a collection of polypeptides containing FKBP domains randomized at the identified positions can be prepared e.g. using conventional synthetic or genetic methods. Such a collection represents a set of FKBP domains containing replacement amino acids at one or more of such positions. The collection is screened and FKBP variants are selected which possess the desired ligand binding properties. In general, randomizing several residues simultaneously is expected to yield compensating mutants of higher affinity and specificity for a given bumped ligand as it maximizes the likelihood of beneficial cooperative interactions between sidechains. Techniques for preparing libraries randomized at discrete positions are known and include primer-directed mutagenesis using degenerate oligonucleotides, PCR with degenerate oligonucleotides, and cassette mutagenesis with degenerate oligonucleotides (see for example Lowman, H. B, and Wells, J. A. *Methods: Comp. Methods Enzymol.* 1991. 3, 205–216; Dennis, M. S. and Lazarus, R. A. 1994. J. Biol. Chem. 269, 22129–22136; and references therein).

In many cases, randomization of only the few residues in or near direct contact with a given position in a ligand may not completely explore all the possible variations in FKBP conformation that could optimally accommodate a ligand substituent (bump). Thus the construction is also envisaged of unbiased libraries containing random substitutions that are not based on structural considerations, to identify subtle mutations or combinations thereof that confer preferential binding to bumped ligands. Several suitable mutagenesis schemes have been described, including alanine-scanning mutagenesis (Cunningham and Wells (1989) Science 244, 1081–1085), PCR misincorporation mutagenesis (see eg. Cadwell and Joyce,1992, PCR Meth. Applic. 2, 28–33), and 'DNA shuffling' (Stemmer, 1994, Nature 370, 389–391 and Crameri et al, 1996, Nature Medicine 2, 100–103). These techniques produce libraries of random mutants, or sets of single mutants, that are then searched by screening or selection approaches.

In many cases, an effective strategy to identify the best mutants for preferential binding of a given bump is a combination of structure-based and unbiased approaches. See Clackson and Wells, 1994, Trends Biotechnology 12, 173–184 (review). For example we contemplate the construction of libraries in which key contact residues are randomized by PCR with degenerate oligonucleotides, but with amplification performed using error-promoting conditions to introduce further mutations at random sites. A further example is the combination of component DNA fragments from structure-based and unbiased random libraries using DNA shuffling.

A further alternative is to clone the randomized ligand-binding domain sequences into a vector for phage display, allowing in vitro selection of the variants that bind best to the ligand. Affinity selection in vitro may be performed in a number of ways. For example, rapalog is mixed with the library phage pool in solution in the presence of recombinant receptor tagged with an affinity handle (for example a hexa-histidine tag, or GST), and the resultant complexes are captured on the appropriate affinity matrix to enrich for phage displaying receptor harboring complementary mutations. Techniques for phage display have been described, and other in vitro selection selection systems can also be contemplated (for example display on lambda phage, display on plasmids, display on baculovirus). Furthermore, selection and screening strategies can also be used to improve other properties of benefit in the application of this invention, such as enhanced stability in vivo. For a review see Clackson, T. and Wells, J. A. 1994. Trends Biotechnol. 12, 173–184.

Antibody subunits, e.g. heavy or light chain, particularly fragments, more particularly all or part of the variable region, or fusions of heavy and light chain to create high-affinity binding, can be used as the binding moiety. Antibodies can be prepared against haptenic molecules which are physiologically acceptable and the individual antibody subunits screened for binding affinity. The cDNA encoding the subunits can be isolated and modified by deletion of the constant region, portions of the variable region, mutagenesis of the variable region, or the like, to obtain a binding protein moiety that has the appropriate affinity for the ligand. In this way, almost any physiologically acceptable haptenic compound can be employed as the ligand or to provide an epitope for the ligand. Instead of antibody units, natural receptors can be employed, where the binding moiety is known and there is a useful ligand for binding.

Transcriptional Modulating Portions (TMP)

The transcriptional modulators of the invention additionally include at least one transcriptional modulating portion (TMP). The language "transcriptional modulating portion" is intended to include a portion which modulates transcription including chemical moieties and proteinaceous domains. The preferred TMPs of the present invention are chemical moieties, e.g., non-peptidyl, small molecules (e.g., having a molecular weight of less than about 1000).

The terms "chemical moiety" or "moiety" are intended to include synthetic and naturally-occurring non-proteinaceous entities. For example, chemical moieties include unsubstituted or substituted alkyl, aromatic, or heterocyclyl moieties including macrolides, leptomycins and related natural products or analogs thereof.

The terms "proteinaceous domain" is intended to include naturally-occurring and nonnaturally-occurring polypeptides. The terms protein, peptide, and polypeptide are used interchangeably herein.

Preferably, the TMP is small having a molecular weight of less than about 5 kD, less than about 4 kD, preferably less than 3 kD, and even more preferably, less than 1.5 kD. When the TMP is a peptide, its amino acid sequence can range in size from about 5 to 30 amino acids, more preferably from about 10 to 25 amino acids, and most preferably from about 15 to 20 amino acids. The peptide can be of a size within a range using any of the above-recited numbers as the upper or lower value of the range.

The transcriptional modulators of the present invention are capable of modulating, e.g., stimulating or inhibiting, transcription of a gene, e.g., a target gene. As used herein, the terms "modulation of transcription" or "regulation of gene expression" or variations thereof are intended to include any changes in gene expression which are triggered directly or indirectly by the transcriptional modulators of the invention, preferably by the transcriptional modulating portion of these transcriptional modulators. For example, changes in gene expression can occur as a result of one or more of: (i) a direct or indirect interaction(s) of the transcriptional modulator with a component of the transcriptional machinery; (ii) an alteration(s) of chromatin structure; and (iii) an alteration(s) in the effective concentration of the transcriptional modulator in the nucleus of a cell.

Figure 1B:
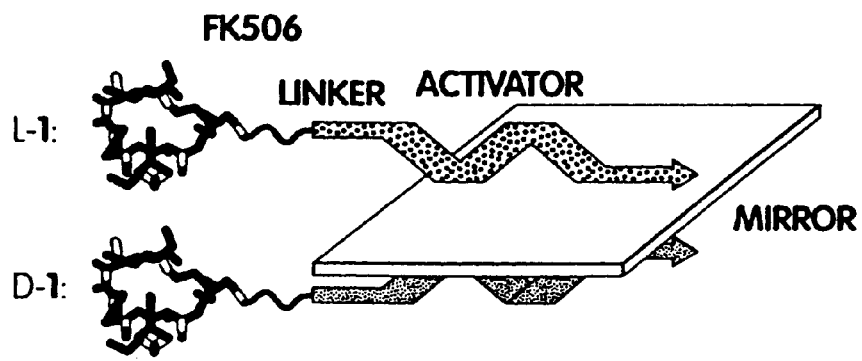
Figure 1C:
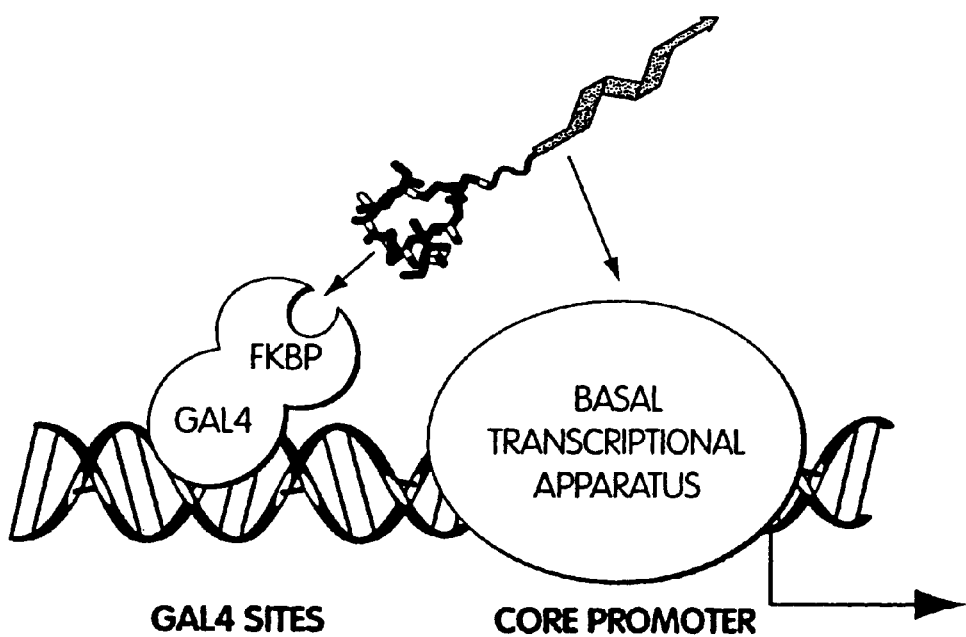

An example of a transcriptional modulator that regulates gene expression via an interaction with a component of the transcriptional machinery is illustrated in schematic form in FIG. 1C. As indicated, the transcriptional modulator is depicted between a DNA-bound chimeric protein (illustrated as GAL4-FKBP) and the basal transcriptional machinery which is bound to the core promoter region. The high affinity interaction between the ligand-binding domain of the chimeric protein (the FKBP illustrated in FIG. 1C) and the transcriptional modulator brings the transcriptional modulating portion in close proximity with the target gene, thus triggering changes in gene expression. The transcriptional modulating portion can include a transcription activator portion, which recruits and/or activates the basal transcription machinery directly or indirectly to result in activation or enhancement of gene expression. Alternatively, the transcriptional modulator portion may include a transcription repressor portion which inhibits or decreases gene expression. Assays for identifying transcriptional modulators which activate or repress transcription activity can be performed using procedures known in the art as exemplified by the Examples provided herein.

An example of a transcriptional modulator that regulates gene expression by altering the chromatin structure occurs when the transcriptional modulator, particularly its transcriptional modulating portion, interacts with chromatin-remodeling and/or modifying complex. In such cases, addition of the transcriptional modulator results in remodeling of the chromatin assembly to, e.g., facilitate assembly of transcription complexes. For example, transcriptional coactivators having intrinsic histone acetyl transferase activity (HATs) have been reported to interact with target histones bound to DNA and overcome the inhibitory effect of chromatin on gene expression (Jenster, G. et al. (1997) *Proc. Natl. Acad. Sci. USA* 94(15): 7879–84). In those instances where transcription activation is desired, the high affinity interaction between the ligand-binding domain of the chimeric protein and the transcriptional modulator can be used to bring the chromatin-remodeling and/or modifying complex in close proximity to the target gene, thus activating gene expression. Alternatively, transcriptional activity may be inhibited by a transcriptional modulator that recruits to the target gene a chromatin-modifying component such that as histone deacetylase such that transcriptional activity is repressed. Assays for detecting changes in chromatin structure and alterations in HAT activity are known in the art. See e.g., Spencer, T. E. et al. (1997) *Nature* 389: 194–8; Jenster, G. et al. (1997) supra; Steger, D. J. et al. (1997) *Methods* 12 (3): 276–85; Steger, D. J. et al (1996) 18(11)).

An example of a transcriptional modulator that regulates gene expression by altering the effective concentration of a complex of a transcriptional modulator and a chimeric protein in the cell nucleus is provided when the transcriptional modulator, preferably, the transcriptional modulating portion, is capable of interacting with a component of the nuclear pore, e.g., a nuclear importer or an exporter, such that the interaction between the transcriptional modulator and the chimeric protein results in translocation of the transcriptional modulator-chimeric protein complex through the nuclear pore. For example, the transcriptional modulator can include a nuclear import or a nuclear export signal, or alternatively a chemical moiety which interacts with a component of the nuclear pore, e.g., e.g., a chemical moiety that interacts with a nuclear exporter, e.g., a member of the leptomycin and kazusamycin family of antibiotics. In such examples, the chimeric protein preferably includes at least one DNA-binding domain, a ligand-binding domain and a transcription modulating domain.

In those embodiments where an increase in the effective concentration of the complex of the transcriptional modulator and the chimeric protein is desired, a chimeric protein is constructed such that it remains in the cytoplasm of a cell. The cell is contacted with a transcriptional modulator which includes, e.g., a nuclear import signal, and thus the complex of the chimeric protein and transcriptional modulator is translocated into the nucleus. Such translocation increases the effective concentration of the chimeric protein in the nucleus. If transcriptional activation is desired, the chimeric protein is constructed such that it contains a transcriptional activation domain. Alternatively, if transcriptional repression is desired, the chimeric protein should contain a transcriptional repressor domain.

In other embodiments, modulation of gene expression can result from a decrease in the effective concentration of a transcriptional modulator. For example, a chimeric protein containing at least one DNA-binding domain, a ligand-binding domain and a transcription modulating domain can be prepared such that it is present in the nucleus. The transcriptional modulating domain can include a transcriptional activating domain, thus resulting in constitutive activation of gene expression. In other embodiments, the transcriptional modulating domain can include a transcriptional repressor domain, thus repressing gene expression. Upon contacting the cell with a transcriptional modulator which includes a nuclear export signal, the complex of the chimeric protein and transcriptional modulator is translocated outside the nucleus. Such translocation decreases the effective concentration of the chimeric protein in the nucleus.

Thus, transcriptional activity will be reduced in those instances where the chimeric protein contains a transcriptional activating domain. Alternatively, transcriptional activity will be increased in those instances where the chimeric protein contains a transcriptional repressor domain. Assays for detecting changes nuclear import-export activity are known in the art. See e.g., Wolff, B. (1997) *Chemistry and Biology,* Vol. 4(2); for a description of an in vitro system using semi-permeabilized cells and a fluorescent import substrate see Paschal, B. M. and Gerace, L. (1995) *J. Cell Biol.* 129: 925–937.

As described above, transcriptional modulators can include chemical moieties and proteinaceous domains. The TMPs (including chemical moieties) also can be designed to form compounds which modulate transcription, e.g., by modelling the TMPs after known transcriptional activators or repressors, nuclear importers or nuclear exporters. In one embodiment, TMPs (in unlinked forms) are screened for a desired activity, e.g., binding (e.g., nuclear export and import), or transcriptional modulation activity. In this embodiment, the TMP is not linked to the selected ligand until after it is identified as a TMP of the present invention.

Exemplary chemical moieties are those identified using the methods provided herein. An additional example of a TMP of the invention which is a chemical moiety is a member of the leptomycin and kazusamycin family of antibiotics. These antibiotics have been shown to bind with high affinity to a component of the nuclear export (Wolff, B. (1997) supra). Members of this family of antibiotics have the general formula as follows:

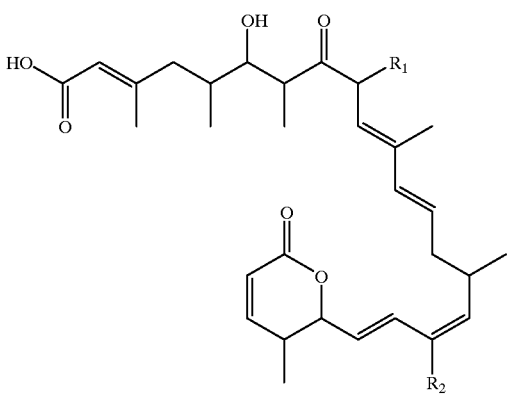

wherein $R_1$ and $R_2$ are each independently selected from a group consisting of a hydrogen, a lower alkyl, an alkyl, a hydroxyalkyl, and a haloalkyl. The term alkyl as herein is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen (including fluoroalkyl), hydroxyl (including hydroxyalkyl). Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 2 or fewer carbon atoms in its backbone. As used herein, the term "halogen" designates —F, —Cl, —Br or —I; the term "sulfhydryl" or "thiol" means —SH; the term "hydroxyl" means —OH. Preferred substitutions of $R_1$ include —$CH_3$ or $CH_2OH$; preferred $R_2$ substitutions include $CH_3$, or $CH_2CH_3$. The TMP can be a member of this family of antibiotics or a structural variant thereof which retains its affinity to bind with a component of the nuclear export.

TMPs can include both naturally occurring and synthetic compounds. In certain embodiments, the TMP is a peptide. The peptide can include one or more amino acids, and preferably all amino acids having either the L- or the D-stereochemistry. Peptides including any combination of amino acids having the L- or D- stereochemistry are encompassed by the invention. Preferred configurations are those which render a peptide more resistant to proteolytic cleavage, as described by the D-configuration of amino acid sequences 1–29 of VP16 provided in the Examples herein. Peptides can be chemically synthesized using techniques known in the art such as conventional Merrifield solid phase f-Moc or t-Boc chemistry. Alternatively, the peptides can be produced recombinantly by standard techniques. Peptide mimetics can also be generated which show enhanced stability. For instance, non-hydrolyzable peptide analogs can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffinan et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and Dann et al. (1986) *Biochem Biophys Res Commun* 134:71).

In some embodiments, the TMP includes a portion of a transcription activator. The transcription activators can be endogenous or exogenous to the cellular host. If the transcription factors are exogenous, but functional within the host and can cooperate with the endogenous RNA polymerase (rather than requiring an exogenous RNA polymerase, for which a gene could be introduced), then an exogenous promoter element functional with the fused transcription factors can be provided with a second construct for regulating transcription of the target gene. By this means the initiation of transcription can be restricted to the gene(s) associated with the exogenous promoter region, i.e., the target gene(s).

Transcriptional activation domains found within various proteins have been grouped into categories based upon similar structural features. Types of transcription activation domains which can be used as TMPs of the present invention include acidic transcription activation domains, proline-rich transcription activation domains, serine/threonine-rich transcription activation domains and glutamine-rich transcription activation domains, and/ or fragments thereof. Examples of acidic transcriptional activation domains include the VP16 amino acid residues 413–490, residues 753–881 of GAL-4. Examples of proline-rich activation domains include amino acids 399–499 of CTF/NF1 and amino acid residues 31–76 of AP2. Examples of serine/threonine-rich transcription activation domains include residues 1–427 of ITF1. Examples of glutamine-rich activation domains include amino acid residues 175–269 of Oct1 and amino acid residues 132–243 of Sp1. The amino acid sequences of each of the above-described regions are disclosed in Seipel, K. et al. (1992) *EMBO J* 13: 4961–4968.

As an alternative to using a naturally-occurring activation domains or modified form thereof, the TMP can be one of the binding proteins associated with bridging between a transcriptional activation domain and an RNA polymerase, including but not limited to RNA polymerase II. These proteins include the proteins referred to as TAF's, the TFII proteins, e.g., TFIIB and TFIID, or the like. Thus, one can use any one or combination of proteins, for example, fused proteins or binding motifs thereof, which serve in the bridge between the DNA binding protein and RNA polymerase and provide for initiation of transcription.

Rather than having a transcriptional activation domain as the TMP, an inactivation domain, such as ssn-6/TUP-1 or Krüppel-family suppressor domain, can be employed as the TMP. In this manner, regulation results in turning off the transcription of a gene which is constitutively expressed. For example, in the case of gene therapy one can provide for constitutive expression of a hormone, such as growth hormone, blood proteins, immunoglobulins, etc. By employing transcriptional repressors as the TMP(s), e.g., ligands covalently linked to an inactivation moiety, the expression of the gene can be inhibited.

Peptide sequences containing nuclear import or export signals can be used ias TNPs in those embodiments where nuclear import or export activity is desired. For example, nuclear import or nuclear localization sequence are known in the art and are known to have a plurality of basic amino acids, referred to as a bipartite basic repeat (reviewed in Garcia-Bustos et al., *Biochimica et Biophysica Acta* (1991) 1071, 83–101; Imamoto, N. ). Examples of nuclear export signals (NES) include leucine-rich amino acid peptide sequences as described in CRMI protein and various viral proteins such as HIV-1 Rev protein, and EIB and E4 proteins(Ossareh-Nazari, B. et al. (1997) *Science* 278: 141–4; Wolff, B. (1997) supra; Dobelstein, M. (1997) EMBO J. 16(4): 4276–84).

Linkers

The linkage between the ligand and the TMP is selected such that the linkage between the (at least two) components of the transcriptional modulator of this invention occurs, and the transcriptional modulator performs its intended function (s). The linker is preferably covalent, either a covalent bond or a linker moiety covalently attached to the ligand moiety and TMP. In certain embodiments, the linker of the invention can a non-covalent bond, e.g., an organometallic bond through a metal center such as platinum atom. For covalent linkages, various functionalities can be used, such as amide groups, including carbonic acid derivatives, ethers, esters, including organic and inorganic esters, amino, urethane, urea, or the like. To provide for linking, the particular ligand monomer can be modified by oxidation, hydroxylation, substitution, reduction, etc., to provide a site for coupling. Depending on the monomer, various sites can be selected as the site of coupling. It will be appreciated that modifications which do not significantly decrease the ability of the ligand to bind to its receptor are preferred.

The ligands can be synthesized by any convenient means, where the linking group will be at a site which allows the formed transcriptional modulator to perform its intended function, e.g., does not interfere with the binding of the binding site of a ligand to the ligand-binding protein, or with the activity of the transcriptional modulating portion. For example, the linker group can be attached to a FK506 derivative, bearing a hydroxyethyl group at C-21, and further attach to an amino acid of a transcriptional modulating portion. Where the active site for physiological activity and binding site of a ligand to the ligand-binding protein are different, it will usually be desirable to link at the active site to inactivate the ligand.

Various linking groups can be employed, usually of from 1–30, more usually from about 1–20 atoms (other than hydrogen) in the chain between the two moieties, where the linking groups will be primarily composed of carbon, hydrogen, nitrogen, oxygen, sulfur and phosphorous. Preferably, the linker is an achiral linker.

The linking groups can involve a wide variety of functionalities, such as amides and esters, both organic and inorganic, amines, ethers, thioethers, disulfides, quaternary ammonium salts, hydrazines, etc. The chain can include aliphatic, alicyclic, aromatic or heterocyclic groups. The chain will be selected based on ease of synthesis and the stability of the ligand-transcriptional modulating moiety. Thus, if one wishes to maintain long-term activity, a relatively inert chain will be used, so that the ligand-transcriptional modulating moiety link will not be cleaved. Alternatively, if one wishes only a short half-life in the blood stream, then various groups can be employed which are readily cleaved, such as esters and amides, particularly peptides, where circulating and/or intracellular proteases can cleave the linking group.

Various groups can be employed as the linking group between ligands, such as alkylene, usually of from 2 to 20 carbon atoms, azalkylene (where the nitrogen will usually be between two carbon atoms), usually of from 4 to 18 carbon atoms), N- alkylene azalkylene (see above), usually of from 6 to 24 carbon atoms, arylene, usually of from 6 to 18 carbon atoms, ardialkylene, usually of from 8 to 24 carbon atoms, bis-carboxamido alkylene of from about 8 to 36 carbon atoms, etc. Illustrative groups include decylene, octadecylene, 3-azapentylene, 5-azadecylene, N-butylene 5 -azanonylene, phenylene, xylylene, p-dipropylenebenzene, bis-benzoyl 1,8-diaminooctane and the like.

Chimeric Proteins

"Recombinant" or "chimeric" proteins, as those terms are used herein, indicate proteins having two or more heterologous domains or portions, e.g., polypeptide domains or sequences which are mutually heterologous in the sense that they do not occur together in the same arrangement in nature. More specifically, the component portions are not found in the same continuous polypeptide or nucleotide sequence or molecule in nature, at least not in the same order or orientation or with the same spacing present in the chimeric protein or recombinant DNA molecule of this invention.

Preferably, the chimeric proteins of the invention have a ligand-binding domain which is capable of binding to a selected ligand molecule and a DNA-binding domain which is capable of binding to a particular DNA sequence(s). The DNA-binding domain may be naturally-occurring or not, including recombinant DNA-binding domain. The chimeric protein may also include one or more linker regions comprising one or more amino acid residues, or include no linker, as appropriate, to join the selected domains.

The chimeric proteins may contain additional domains. For example, chimeric proteins used in the nuclear translocation mechanism for controlling transcriptional regulation described above may additionally contain a transcriptional modulatory domain, e.g., a transcriptional activation or repressor domain.

Such chimeric proteins and DNA sequences which encode them are recombinant in the sense that they contain at least two constituent portions which are not otherwise found directly linked (covalently) together in nature, at least not in the order, orientation or arrangement present in the recombinant material. Desirable properties of the chimeric proteins of the invention include high affinity for specific nucleotide sequences, low affinity for most other sequences in a complex genome (such as a mammalian genome), and low dissociation rates from specific DNA sites. Preferably, the DNA-binding domains bind to a particular DNA sequence(s) with high affinity, preferably with a dissociation constant below about $10^{-9}$M, more preferably below about $10^{-10}$M, even more preferably below $10^{-11}$M.

The choice of DNA-binding domains may be influenced by a number of considerations, including the species, system and cell type which is targeted; the feasibility of incorporation into a chimeric protein, as may be shown by modeling; and the desired application or utility. The choice of DNA-binding domains may also be influenced by the individual DNA sequence specificity of the domain and the ability of the domain to interact with other proteins or to be influenced by a particular cellular regulatory pathway. Preferably, the distance between domain termini is relatively short to facilitate use of the shortest possible linker or no linker. The DNA-binding domains can be isolated from a naturally-occurring protein, or may be a synthetic molecule based in whole or in part on a naturally-occurring domain.

As used herein, a "DNA-binding domain" refers to a molecule, e.g., a protein, which binds to a specific DNA sequence(s). The DNA binding domain of the chimeric protein may be derived from any vertebrate, nonvertebrate, fingal, plant, or bacterial source including but not limited to GAL4 (Keegan et al. (1986) *Science* 231: 699–704), ADR1 (Hartshorne et al. (1986) *Nature* 320: 283–287), SwI (Stillman et al. (1988) *EMBO J* 7: 485–495) and as generally reviewed in Johnson et al. (1989) *Ann. Rev. Biochem.* 58: 799–839). It may be a repressor protein such as, for example, the Lex A. DNA-binding domains found in various proteins have been grouped into categories based upon similar structural featurs. Such types of DNA binding domains are recognized in the art, such as zinc fingers (Miller et al. (1985) EMBO J. 4: 1609), homeodomains (Scott et al., *Biochim. Biophys. Acta* 989:25–48 (1989) and Rosenfeld, *Genes Dev.* 5:897–907 (1991)).

Chimeric constructs encoding chimeric proteins can optionally contain cellular targeting sequences, e.g., signal consensus sequence, which provide for the protein to be translocated to the nucleus. As described above, this "signal consensus" sequence has a plurality of basic amino acids, referred to as a bipartite basic repeat (reviewed in Garcia-Bustos et al., *Biochimica et Biophysica Acta* (1991) 1071, 83–101). This sequence can appear in any portion of the molecule internal or proximal to the N- or C-tenninus and results in the chimeric protein being transported inside the nucleus. However, in those embodiments in which transcriptional activity is regulated by nuclear translocation, i.e., nuclear import, the chimeric protein will not contain such signal consensus sequence.

Nucleotide sequences encoding chimeric proteins can be placed under the control of a suitable promoter sequence. It may be desirable for the nucleotide sequences encoding chimeric protein to be placed under the control of a constitutively active promoter sequence, although the chimeric protein may also be placed under the control of an inducible promoter, such as the metallothionine promoter (Brinster et al., 1982, Nature 296:39–42) or a tissue specific promoter. Promoter sequences which may be used according to the invention include, but are not limited to, the SV40 early promoter region (Bernoist and Chambon, 1981, Nature 290:304–310), the promoter contained in the long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445) the human cytomegalovirus (CMV) immediate early promoter/enhancer (Boshart et al., 1985, Cell 41:521–530).

It will be preferred in certain embodiments, that the chimeric proteins be expressed in a cell-specific or tissue-specific manner. Such specificity of expression may be achieved by operably linking one ore more of the DNA sequences encoding the chimeric protein(s) to a cell-type specific transcriptional regulatory sequence (e.g. promoter/enhancer). Numerous cell-type specific transcriptional regulatory sequences are known. Others may be obtained from genes which are expressed in a cell-specific manner. See e.g. PCT/US95/10591, especially pp. 36–37.

For example, constructs for expressing the chimeric proteins may contain regulatory sequences derived from known genes for specific expression in selected tissues. Representative examples are tabulated below:

| Tissue | Gene | Reference |
| --- | --- | --- |
| lens | γ2-crystallin | Breitman, M.L., Clapoff S., Rossant, J., Tsui, L.C., Golde, L.M., Maxwell, I.H., Bernstin, A. (1987) Genetic Ablation: targeted expression of a toxin gene causes microphthalmia in transgenic mice. Science 238: 1563–1565 |
|  | αA-crystallin | Landel, C.P., Zhao, J., Bok, D., Evans, G.A. (1988) Lens-specific expression of a recombinant ricin induces developmental defects in the eyes of transgenic mice. Genes Dev. 2: 1168–1178 |
|  |  | Kaur, S., key, B., Stock, J., McNeish, J.D., Akeson, R., Potter, S.S. (1989) Targeted ablation of alpha-crystallin-synthesizing cells produces lens-deficient eyes in transgenic mice. Development 105: 613–619 |
| pituitary - somatrophic cells | Growth hormone | Behringer, R.R., Mathews, L.S., Palmiter, R.D., Brinster, R.L. (1988) Dwarf mice produced by genetic ablation of growth hormone-expressing cells. Genes Dev. 2: 453–461 |
| pancreas | Insulin- Elastase - acinar cell specific | Ornitz, D.M., Palmiter, R.D., Hammer, R.E., Brinster, R.L., Swift, G.H., MacDonald, R.J. (1985) Specific expression of an elastase-human growth fusion in pancreatic acinar cells of transgeneic mice. Nature 131: 600–603 |
|  |  | Palmiter, R.D., Behringer, R.R., Quaife, C.J., Maxwell, F., Maxwell, I.H., Brinster, R.L. (1987) Cell lineage ablation in transgeneic mice by cell-specific expression of a toxin gene. Cell 50: 435–443 |
| T cells | lck promoter | Chaffin, K.E., Beals, C.R., Wilkie, T.M., Forbush, K.A., Simon, M.I., Perlmutter, R.M. (1990) EMBO Journal 9: 3821–3829 |
| B cells | Immunoglobulin kappa light chain | Borelli, E., Heyman, R., Hsi, M., Evans, R.M. (1988) Targeting of an inducible toxic phenotype in animal cells. Proc. Natl. Acad. Sci. USA 85: 7572–7576 |
|  |  | Heyman, R.A., Borrelli, E., Lesley, J., Anderson, D., Richmond, D.D., Baird, S.M., Hyman, R., Evans, R.M. (1989) Thymidine kinase obliteration: creation of transgenic mice with controlled immunodeficiencies. Proc. Natl. Acad. Sci. USA 86: 2698–2702 |

-continued

| Tissue | Gene | Reference |
|---|---|---|
| Schwann cells | P₀ promoter | Messing, A., Behringer, R.R., Hammang, J.P. Palmiter, RD, Brinster, RL, Lemke, G.,P₀ promoter directs espression of reporter and toxin genes to Schwann cells of transgenic mice. Neuron 8: 507–520 1992 |
| | Myelin basic protein | Miskimins, R. Knapp, L., Dewey,MJ, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M.L., Rombola, H., Maxwell, I.H., Klintworth, G.K., Bernstein, A. (1990) Genetic ablation in transgenic mice with attenuated diphtheria toxin A gene. Mol. Cell. Biol. 10: 474–479 |
| lung | Lung surfacant gene | Ornitz, D.M., Palmiter, R.D., Hammer, R.E., Brinster, R.L., Swift, G.H., MacDonald, R.J. (1985) Specific expression of an elastase-human growth fusion in pancreatic acinar cells of transgeneic mice. Nature 131: 600–603 |
| adipocyte P2 | | Ross, S.R, Braves, RA, Spiegelman, BM Targeted expression of a toxin gene to adipose tissue: transgenic mice resistant to obesity Genes and Dev 7: 1318–24 1993 |
| muscle | myosin light chain | Lee, KJ, Ross, RS, Rockman, HA, Hanis, AN, O'Brien, TX, van-Bilsen, M., Shubeita, HE, Kandolf, R., Brem, G., Prices et alJ. BIol. Chem. 1992 Aug 5, 267: 15875–85 |
| | Alpha actin | Muscat, GE., Perry, S. , Prentice, H. Kedes, L. The human skeletal alpha-actin gene is regulated by a muscle-specific enhancer that binds three nuclear factors. Gene Expression 2, 111–26, 1992 |
| neurons | neurofilament proteins | Reeben, M. Halmekyto, M. Alhonen, L. Sinervirta, R. Saarma, M. Janne,J. Tissue-specific expression of rat light neurofilament promoter-driven reporter gene in transgenic mice. BBRC 1993: 192: 465–70 |
| liver | tyrosine aminotransferase, albumin, apolipoproteins | |

Additional examples of tissue-specific regulatory sequences include Elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinker et al. 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in erytlroid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985; Nature 314:283–286), and gonadotropic releasing hormone gene control region which is active in hypothalamus (Mason et al., 1986, Science 234:1372–1378).

A detailed description of DNA constructs encoding these chimeric proteins (and accessory constructs such as DNA constructs encoding target genes) is provided in the section entitled "Genes and Vectors" below.

Genes and Vectors

Recombinant nucleic acid molecules containing target genes and nucleotide sequences encoding the chimeric proteins are provided, as are vectors capable of directing their expression, particularly in eukaryotic cells, of which yeast and animal cells are of particular interest. In view of the constituent components of the chimeric proteins, the recombinant nucleic acid molecules which encode them are capable of selectively hybridizing (a) to a DNA molecule encoding a given chimeric protein's ligand-binding domain (e.g., FRB domain or FKBP domain) or a protein containing such a domain and (b) to a DNA molecule encoding the heterologous domain or a protein from which the heterologous protein domain was derived, e.g., a DNA-binding domain. DNAs are also encompassed which would be capable of so hybridizing but for the degeneracy of the genetic code.

In the present specification, the terms "plasmid", "vector" or "construct" are used interchangeably. As used herein, these terms refer to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/ expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. However, the invention is intended to include such other forms of expression vectors which serve equivalent functions and which become known in the art subsequently hereto.

The constructs of the invention can be introduced as one or more DNA molecules or constructs, where there will usually be at least one marker and there may be two or more markers, which will allow for selection of host cells which contain the construct(s). The constructs can be prepared in conventional ways, where the genes and modulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagensis, etc. as appropriate. The construct(s) once completed and demonstrated to have the appropriate sequences may then be introduced into the host cell by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells will usually be grown and expanded in culture before introduction of the construct(s), followed by the appropriate treatment for introduction of the construct(s) and integration of the construct(s). The cells will then be expanded and screened by virtue of a marker present in the construct. Various markers which may be used successfully include hprt, neomycin resistance, thymidine kinase, hygromycin resistance, etc.

In some instances, one may have a target site for homologous recombination, where it is desired that a construct be integrated at a particular locus. For example, can knock-out an endogenous gene and replace it (at the same locus or elswhere) with the gene encoded for by the construct using materials and methods as are known in the art for homologous recombination. Alternatively, instead of providing a gene, one may modify the transcriptional initiation region of an endogenous gene to be responsive to the signal initiating moiety. In such embodiments, transcription of an endogenous gene such as EPO, tPA, SOD, or the like, would be controlled by administration of the ligand. For homologous recombination, a number of vectors can be used. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, etc. which may be used to prepare stocks of construct DNAs and for carrying out transfections are known in the art, and many are commercially available.

IV. Pharmaceutical Compositions

In another aspect, the present invention provides pharmaceutically acceptable compositions which comprise a therapeutically-effective amount of one or more of the transcriptional modulators of the present invention, formulated together with one or more pharmaceutically acceptable carrier(s). The pharmaceutical compositions and methods described herein can include one or more transcriptional modulators of the present invention. Any combination of these transcriptional modulators (e.g., transcriptional modulators which result in activation of gene expression by any of the mechanisms (i)–(iii)) is intended to be encompassed by the present invention.

The phrase "therapeutically-effective amount" as used herein means that amount of a transcriptional modulators, or composition comprising such a compound which is effective for the transcriptional modulator to produce its intended function, e.g., the modulation of gene expression. The effective amount can vary depending on such factors as the type of cell growth being treated or inhibited, the particular type of transcriptional modulator, the size of the subject, or the severity of the undesirable cell growth or activity. One of ordinary skill in the art would be able to study the aforementioned factors and make the determination regarding the effective amount of the transcriptional modulator without undue experimentation.

The phrase "pharmaceutically acceptable" is employed herein to refer to those transcriptional modulators, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Transcriptional modulators of the present invention can exist in free form or, where appropriate, in salt form. Pharmaceutically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the transcriptional modulator, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The transcriptional modulator can be a liquid solution, suspension, emulsion, tablet, pill, capsule, sustained release formulation, or powder. The transcriptional modulator can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet- disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions ,and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The transcriptional modulator can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of a transcriptional modulator may be dissolved in an aqueous solution of an organic or inorganic acid, such as a 0.3 M solution of succinic acid or citric acid. Alternatively, acidic derivatives can be dissolved in suitable basic solutions. If a soluble salt form is not available, the compound is dissolved in a suitable cosolvent or combinations thereof Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the transcriptional modulator, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the transcriptional modulator locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the transcriptional modulator is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. In embodiments in which the transcriptional modulator includes a ligand. e.g., rapamycin or a derivative thereof, with some residual immunosuppressive effects, it is preferred that the dose administered be below that associated with undue immunosuppressive effects.

The amount of compound which will be effective in the treatment or prevention of a particular disorder or condition will depend in part on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a transcriptional modulator, drug or other material, such that it enters the subject's system and, thus, is subject to metabolism and other like processes, for example, subcutaneous administration.

The invention also provides a pharmaceutical package or kit comprising one or more containers filled with one or more of the ingredients of the pharmaceutical compositions of the invention. Optionally associated with such container (s) can be a notice in the form prescribed by a govermnental agency regulating the manufacture, use or sale of pharmaceutical or biological products, which notice reflects approval by the agency of manufacture, use or sale for human administration. The package also can include instructions for using the transcriptional modulator within the methods of the invention.

Administration of Cells and Transcriptional Modulators

The genetically modified cells can be grown in culture under selective conditions and cells which are selected as having the construct may then be expanded and further analyzed, using, for example, the polymerase chain reaction for determining the presence of the construct in the host cells. Once the modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$, more usually not more than about $10^8$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the burn or other lesion. Generally, for myoblasts or fibroblasts, the number of cells will at least about $10^4$ and not more than about $10^8$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213–24 (HepG2 cells/hydroxyethyl methacrylate-methyl methacrylate membranes); Chang et al, 1993, Hum Gene Ther 4(4):433-40 (mouse Ltk—cells expressing hGH/immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23):10898–902 (polymer-encapsulated engineered BHK cells expressing HNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of virus vectors have been developed, such as adenovirus and retroviruses, which allow for transfection and random integration of the virus into the host. See, for example, Dubensky et al. (1984) Proc. Natl. Acad. Sci. USA 81, 7529–7533; Kaneda et al., (1989) Science 243, 375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Depending upon the binding affinity of the transcriptional modulator, the response desired, the manner of administration, the half-life, the number of cells present, various protocols may be employed. The transcriptional modulator may be administered parenterally or orally. The number of administrations will depend upon the factors described above. The transcriptional modulator may be taken orally as a pill, powder, or dispersion; bucally; sublingually; injected intravascularly, intraperitoneally, subcutaneously; by inhalation, or the like. The transcriptional modulator (and free monomeric antagonist) may be formulated using conveniotnal methods and materials well known in the art for the various routes of administration. The precise dose and particular method of administration will depend upon the above factors and be determined by the attending physician or human or animal healthcare provider. For the most part, the manner of administration will be determined empirically.

In the event that the activation by the transcriptional modulator is to be reversed, the free monomeric compound may be administered or other single binding site compound which can compete with the transcriptional modulator. Thus, in the case of an adverse reaction or the desire to terminate the therapeutic effect, the monomeric binding compound can be administered in any convenient way, particularly intravascularly, if a rapid reversal is desired. Alternatively, one may provide for the presence of an inactivation domain with a DNA binding domain, or apoptosis by having Fas or TNF receptor present as constitutively expressed constructs.

The particular dosage of the transcriptional modulator for any application may be determined in accordance with the procedures used for therapeutic dosage monitoring, where maintenance of a particular level of expression is desired over an extended period of times, for example, greater than about two weeks, or where there is repetitive therapy, with individual or repeated doses of transcriptional modulator over short periods of time, with extended intervals, for example, two weeks or more. A dose of the transcriptional modulator within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the transcriptional modulator is chronically administered, once the maintenance dosage of the transcriptional modulator is determined, one could then do assays at extended intervals to be assured that the cellular system is providing the appropriate response and level of the expression product.

The subject methodology and compositions may be used for the treatment of a wide variety of conditions and indications. For example, B- and T-cells may be used in the treatment of cancer, infectious diseases, metabolic deficiencies, cardiovascular disease, hereditary coagulation deficiencies, autoimmune diseases, joint degenerative diseases, e.g. arthritis, pulmonary disease, kidney disease, endocrine abnormalities, etc. Various cells involved with structure, such as fibroblasts and myoblasts, may be used in the treatment of genetic deficiencies, such as connective tissue deficiencies, arthritis, hepatic disease, etc. Hepatocytes could be used in cases where large amounts of a protein must be made to complement a deficiency or to deliver a therapeutic product to the liver or portal circulation.

Applications

1. Regulated gene therapy. In many instances, the ability to switch a therapeutic gene on and off at will or the ability to titrate expression with precision are important for therapeutic efficacy. This invention is particularly well suited for achieving regulated expression of a therapeutic target gene in the context of human gene therapy. As described in detail in the section entitled "Transcriptional Modulating Portion", the transcriptional modulators of the present invention can act in a genetically engineered cell (e.g., a cell genetically modified to contain at least one chimeric protein and/or at least one target gene) by one or more of (i) a direct or indirect interaction(s) of the transcriptional modulator with a component of the transcriptional machinery; (ii) an alteration(s) of chromatin structure; and (iii) an alteration(s) in the effective concentration of the transcriptional modulator in the nucleus of a cell. Contacting the engineered cells or the progeny thereof with the transcriptional modulators (by administering the agent to the subject) leads to expression of the target gene. In practice, the level of target gene expression should be a function of the number or concentration of chimeric protein-transcriptional modulator complexes, which should in turn be a function of the concentration of the transcriptional modulator.

The transcriptional modulator may be administered to the patient as desired to activate transcription of the target gene. Depending upon the binding affinity and activity of the transcriptional modulator, the response desired, the manner of administration, the half-life, the number of cells present, various protocols may be employed. The transcriptional modulator may be administered parenterally or orally. The number of administrations will depend upon the factors described above. The ligand may be taken orally as a pill, powder, or dispersion; bucally; sublingually; injected intravascularly, intraperitoneally, intramuscularly, subcutaneously; by inhalation, or the like. The ligand (or antagonist) may be formulated using conventional methods and materials known in the art for the various routes of administration. The precise dose and particular method of administration will depend upon the above factors and be determined by the attending physician. For the most part, the manner of administration will be determined empirically.

In the event that transcriptional activation by the transcriptional modulator is to be reversed or terminated, compound which can compete with the transcriptional modulator may be administered. Alternatively, combinations of the transcriptional modulators of the present invention can be used to control gene expression. For example, combinations of transcriptional activators containing a transcriptional activator portion or a transcriptional repressor portion can be used. Thus, in the case of an adverse reaction or the desire to terminate the therapeutic effect, an antagonist to the transcriptional modulator can be administered in any convenient way, particularly intravascularly, if a rapid reversal is desired. In another approach, cells may be eliminated through apoptosis via signalling through Fas or TNF receptor as described elsewhere. See International Patent Applications PCT/US94/01617 and PCT/US94/08008.

The particular dosage of the transcriptional modulator for any application may be determined in accordance with the procedures used for therapeutic dosage monitoring, where maintenance of a particular level of expression is desired over an extended period of times, for example, greater than about two weeks, or where there is repetitive therapy, with individual or repeated doses of transcriptional modulator over short periods of time, with extended intervals, for example, two weeks or more. A dose of the transcriptional modulator within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

2. Production of recombinant proteins and viruses. Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

3. Biological research. This invention is applicable to a wide range of biological experiments in which precise control over a target gene is desired. These include: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of chimeric proteins of this invention and, in embodiments involving regulated gene transcription, a target gene construct containing a target gene linked to one or more transcriptioal control elements which are activated by the transcriptional modulator-chimeric protein complex. Alternatively, the target gene construct may contain a cloning site for insertion of a desired target gene by the practitioner. Such kits may also contain a sample of a small molecule of transcriptional modulator, or any combination of transcriptional modulators.

The practice of the present invention employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

EXAMPLES

The invention now being generally described, it will be more readily understood by reference to the following examples which are included merely for purposes of illustration of certain aspects and embodiments of the present invention, and are not intended to limit the invention.

Synthesis of Transcriptional Modulators (Non-natural Coactivator L-1 and D-1)

The synthesized transcriptional modulators and techniques described below were used in the Examples.

The Boc-protected hexarnethylenediamine carbamate derivative of FK506 was deprotected and N-bromoacetylated in situ by treatment with bromoacetic anhydride as described in Robey, F. A. and Fields, R. L., *Anal. Biochem.,* 177:373–377 (1989). The product was purified by flash chromatography and its structure was confirmed by fast atom bombardment-HRMS. The L and D activator peptides CGSDALDDFDLDMLGSDALD-DFDLDMLGS-NH$_2$ (SEQ ID NO:1) were synthesized by standard solid phase peptide synthesis (rink resin)/deprotection methods, purified by reversed-phase HPLC, and characterized by amino acid analysis and HRMS. The bromoacetylated FK506 derivative and activator peptide were coupled using a procedure reported for protein ligation [Muir, T. W., et al., *Biochemistry,* 33:7702–7708 (1994)]. Briefly, the activator peptide (650 µg, 0.21 µmol) was combined with bromoacetylated-FK506 (250 µg 0.23 µmol) in 300 µl of 95% dimethyl-formamide/5% 0.1M sodium phosphate buffer (pH 7) and the reaction was allowed to proceed overnight at room temperature. The product was purified by anion-exchange chromatography on a Waters Gen-Pack FAX HPLC column (4.6×100 mm) using a gradient of 5–45% B over 40 min (eluent A: 25 mM Tris-HCl, pH 7.5/10% CH$_3$CN; eluent B: eluent A+1.0 M NaCl). After desalting on a C$_{18}$ Waters Sep-Pack Cartridge, the product was eluted with 9:1 acetonitrile/water and lyophilized. L-1 and D-1 conjugates were quantified by amino acid analysis and characterized by electrospray-ionization mass spectroscopy (negative ion absorption mode).

In Vitro Transcription. HeLa nuclear extracts were prepared as described in Dignam, J. D., et al., *Nucleic Acids Res.,* 11:1475–1489 (1983). GAL4(1–147)-VP16(413–490) was overexpressed and purified as described [Chasman, D. J., et al., *Mol. Cell. Biol.,* 9:4746–4749 (1989)]. The expression vectors coding for GAL4(1–94), and GAL4(1–94). FKBP12 were sub-cloned into pI.M1 [Sodcoka, M., et al., *Bioorganic. Med. Chem. Lett.,* 3:1089–1094 (1993)] and the resulting fusion proteins were overexpressed and purified to homogeneity essentially as described for GAL4(1–147)-VP16 (413–490). In vitro transcription assays were performed as described in Carey, M., et al., *Science,* 247:710–712 (1990). The mixtures contained 25 µl of HeLa nuclear extract (3.15 mg/ml) in Dignam D buffer (20 mM Hepes, pH 7.9/100 mM KCl/20% glycerol/0.2 mM EDTA/0.5 mM DTT/0.5 mM phenylmethylsufonyl fluoride), 8 mM MgCl$_2$, 10 mM ammonium sulfate, 1% PEG 8000, 0.1 mg/ml BSA, 8 units RNA guard, 200 ng of 1% PEG 8000, 0.1 mg/ml BSA, 8 units RNA guard, 200 ng of pGEM3 as carrier, 30 ng of template pG$_5$E4T and either no GAL4 protein or an amount sufficient to give >90% protein-DNA complex, as determined by independent gel-shift assays. The optimal amount of compounds L-1 and D-1 was titrated by transcription in vitro. GAL4-FKBP was preincubated 10 min at room temperature with 10 molar equivalents of coactivator L-1 or D-1 followed by a 10 min incubation time with the reporter template. After addition of the nuclear extract and further preincubation for 15 min at room temperature, the reaction was initiated by addition of 2 µl of rNTP mix 10 mM. After 1 h at 30° C., the reaction was terminated and the reaction products were purified and analyzed by primer extension as described [Carey, M., et al., *Science,* 247:710–712 (1990)]. Each experiment was repeated a minimum of three times.

In Vitro Transcription. Jurkat cells were maintained in RPMI 1640 media containing 10% (vol/vol) calf serum, L-glutamine and 1% (vol/vol) penicillin/streptomycin. Cells plated in a six-well tissue culture plate (2×10$^6$ cells per well) were transfected (6 µl DMRIE-C; GIBCO/BRL) with 2 µg each of G5IL2SX and GF$_3$. After 24 h incubation, the medium was removed and the cells were resuspended in fresh Opti-Mem I reduced serum medium and atiquoted into a 96-well microtiter plate (2×10$^6$ cells per well). Various concentrations of L-1 and D-1 in DMRIE-C were added to the cells. After 24 h, aliquots were removed and assayed for secreted alkaline phosphatase (SEAP) activity as described in Belahaw, P. J., et al., *Proc. Natl. Acad. Sci. USA,* 93:4604–4607 (1996). In competition experiments, 1 µM rapamycin was added at the same time as D-1.

A molecule designed to serve as an intermediary between a DNA-binding protein and the transcriptional apparatus should incorporate binding elements for each of these two macromolecular targets. In order to meet this criterion, the immunosuppresive drug FK506, which binds with high affinity ($K_d$=0.4 nM) to the immunophilin FK binding protein 12 (FKBP12) was chosen [Standaert, R. F., et al., *Nature* (London), 346:671–674 (1990). FK506 and certain derivatives thereof can be targeted to the DNA binding domain of GAL4 by fusing the GAL4 domain to FKBP (GAL4-FKBP) [Belahaw, P. J., et al., *Proc. Natl. Acad. Sci. USA,* 93:4604–4607 (1996)]. Modification of the calcineurin-binding surface of FK506 yields derivatives that lack immunosuppressive properties but retain the ability to bind FKBP with high affinity [Belahaw, P. J., et al., *Proc. Natl. Acad. Sci. USA,* 93:4604–4607 (1996); Bierer, B. E., et al., *Science,* 250:556–559 (1990)]. The nonimimunosuppressive FK506 derivative, bearing a hydroxyethyl group at C-21, was further equipped with an activator element through the addition of a linker, to which a transcriptional activation domain was attached. In particular, a 29-amino acid L peptide containing a tandemly repeated undecamer sequence derived from the N-terminal portion of the VP16 activation domain was attached (FIGS. 1A and B). This L peptide, when directly fused to the GAL4 DNA-binding domain, is a potent activator of transcription in vivo [Seipel, K., et al., *EMBO J*, 11:49614968 (1992)], most likely through binding directly to component(s) of the basal transcriptional apparatus [Lin, Y. -S, et al., *Nature* (London), 353:569–571 (1991)]. Thus, the FK506-peptide conjugate L-1 could in principle be capable of bridging GAL4-FKBP and the basal transcriptional apparatus (FIG. 1C).

Example I
In Vitro Modulation of Transcription Using Transcriptional Modulators

Figure 2A:
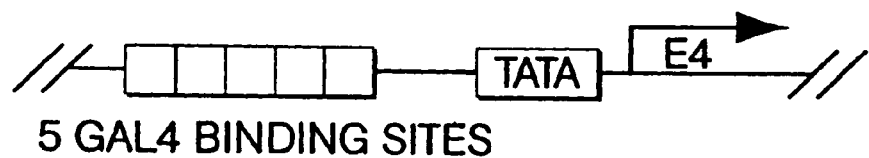
FIG. 2A is a schematic representation of the target gene pG$_5$FAT which contains five tandem 17-bp GAL4 binding sites (indicated by open boxes) positioned 23 bp upstream to the TATA box of a E4 promoter gene.
Figure 2B:
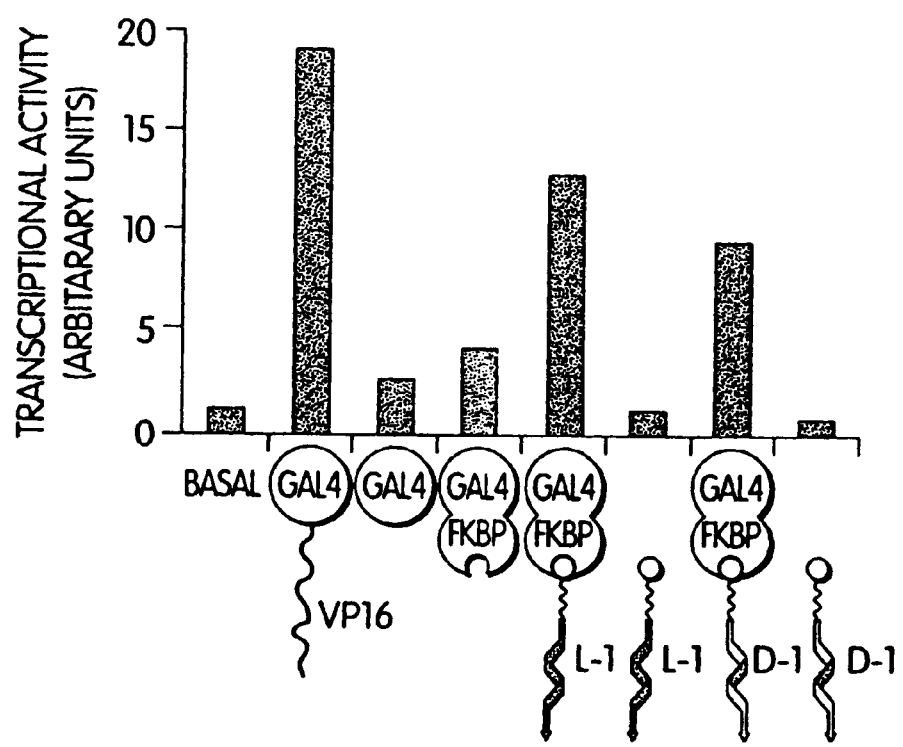
FIG. 2B is a bar graph which summarizes the quantitation of the in vitro transcription assays using the transcriptional modulators (transcriptional activators L-1 and D-1). The template pG$_5$ E4T was transcribed in a crude HeLa cell nuclear extract in the presence of various added proteins and activators as indicated. The transactivator's activity is plotted relative to the activity of the control nuclear extract.
Figure 3A:
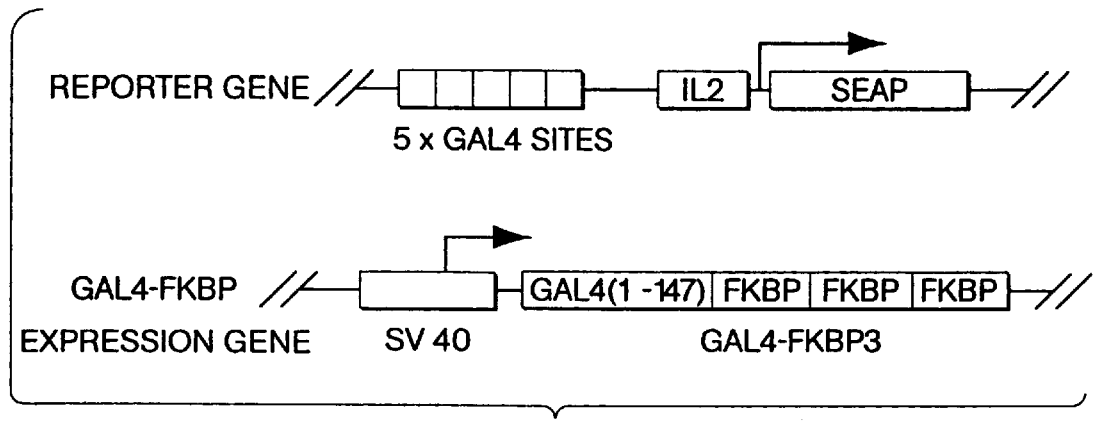
FIG. 3A is a schematic representation of the target plasmids and the GAL4-FKBP3 expression constructs transfected into Jurkat cells in these examples. The target construct (Top) G5IL2SX contains five tandem copies of the GAL4 response element upstream of the interleukin 2 minimal promoter and SEAP target; the GAL4-FKBP3 expression construct contains the GAL4 DNA-binding domain fused to three tandemly repeated FKBP domains (Bottom).
Figure 3B:
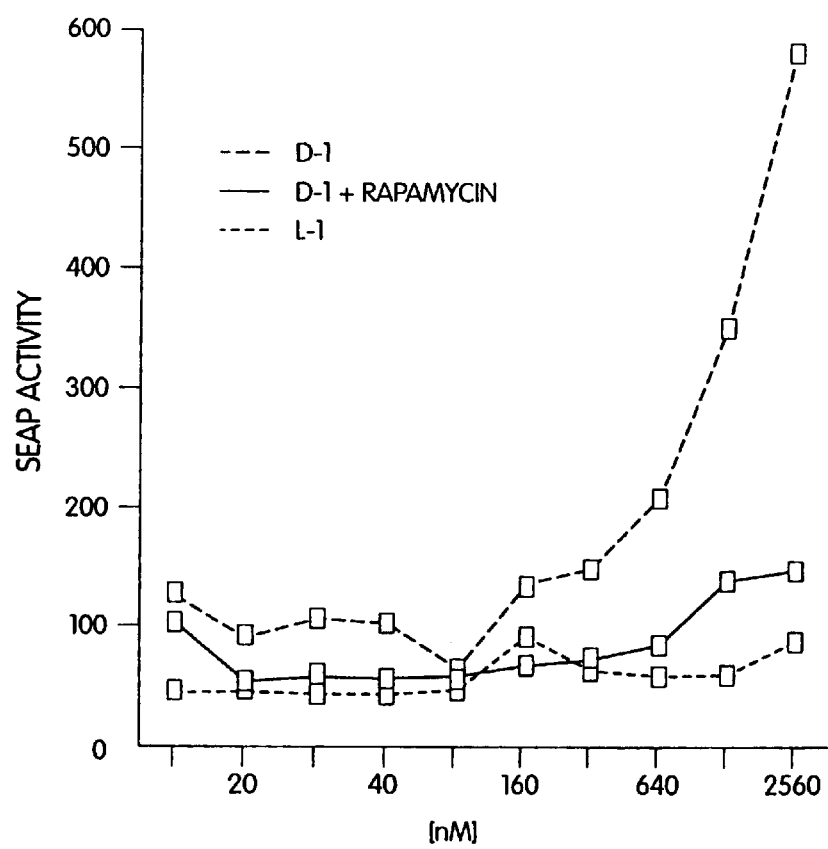
FIG. 3B is a graph depicting the results of in vivo transcription experiments using the activators D-1 and L-1 in the presence of the competitor rapamycin (1 μM).

To assess the ability of L-1 to function as a transcriptional coactivator, in vitro transcription assays using HeLa nuclear extracts and a reporter gene pG$_5$E4T containing 5 GAL4 sites upstream of an adenovirus E4 promoter were carried out (FIGS. 2–3B). As shown in FIG. 2B (lane 5), L-1 stimulated transcription in the presence of GAL4-FKBP, but was unable to stimulate in the absence of GAL4-FKBP (lane 6). The activation potential of L-1 was significantly reduced in the presence of added rapamycin or GST-FKBP. These molecules are known to compete with the L-1/GAL4-FKBP interaction [Bierer, R. F., et al., *Proc. Natl. Acad Sci. USA*, 87:9231–9235 (1990)]. The competition assays were carried out as described (Carey, M. et al. (1990) *Science* 247, 710–712), except GAL4-FKBP was preincubated 10 min at room temperature with 10 equivalents of compound L-1 or D-1 plus 100 equivalents of competitor (rapamycin), prior to the addition of the reporter template and the HeLa nuclear extract. FKBP12 was expressed in *Escherichia coli* as a glutathione 5-transferase fusion protein and purified on glutathion agarose beads. These experiments demonstrate that L-1 functions as a coactivator with GAL4-FKBP in vitro.

Acyclic peptides having the natural L stereocheinical configuration are highly susceptible to proteolysis, in vivo, especially when they possess unmodified amide bonds [Saffran, M., et al., *Science*, 233:1081–1084 (1986)]. For this reason, it seemed unlikely that L-1 would function effectively to activate transcription in cells. On the other hand, peptides bearing the nonnatural D stereochemistry are often resistant to proteolysis, even in linear form [Wermuth, J., et al., *J. Am. Chem. Soc.*, 119:1328–1335 (1997)]. However, it is unknown whether a D configured peptide, or for that matter any nonnatural ligand, can function as a transcriptional activator. To test this whether a D configured peptide can function as a transcriptional activator, an FK506 conjugate bearing the enantiomeric, D configured version of the VP16 activation peptide was used. This conjugate is referred to herein as D-1 (FIGS. 1B and C). The results of in vitro transcription assays demonstrate that D-1 reproducibly stimulated transcription to a significant extent, though to a slightly lesser extent than L-1 (FIG. 2, lane 7). D-1exhibited no activation in the absence of GAL4-FKBP (lane 8), and its activation potential was significantly reduced in the presence of added rapamycin or gluthione S-transferase-FKBP. These results establish that the nonnatural molecule D-1 functions effectively as a transcriptional coactivator in vitro.

Example II
In Vivo Modulation of Transcription Using a Synthetic Transcriptional Modulators To determine whether D-1 can function as a coactivator of transcription in living cells, Jurkat cells were transiently cotransfected with (i) a reporter plasmid containing the SEAP cDNA and an interleukin 2 promoter with five upstream GAL4 DNA binding sites, and (ii) a constitutive expression plasmid encoding the GAL4 DNA-binding domain fused to three tandemly repeated FKBP12s modules (GAL4-FKBP3, FIG. 3). The transfected cells were subsequently treated with various concentrations of L-1 and D-1 incorporated into liposomes to enhance cell-permeability. When the cells were treated with D-1, expression of the SEAP reporter gene was stimulated in a dose-dependent manner (FIG. 3B). When the GAL4-FKBP3 expression plasmid was omitted during the transfection step, the cells were unresponsive to D-1, indicating that the activation stimulus was dependent upon a interaction between GAL4-FKBP3 and D-1. Consistent with this, rapamycin abolished the activation signal, presumably by competing with the FK506 portion of D-1 for the FKBP domain in GAL4-FKBP3. By contrast, L-1 showed no detectable ability to activate SEAP expression in transfected cells (FIG. 3B). As the L activation peptide is known to stimulate transcription in HeLa [Seipel, K., et al., *EMBO J.*, 11:4961–4968 (1992)] and Jurkat cells when fused to the GAL4DNA binding domain, and as FK506 derivatives are capable of saturating FKBP binding sites under the conditions of these experiments [Belshaw, P. J., et al., *Proc. Natl. Acad. Sci. USA*, 93:4604–4607 (1996); Ho, S. H., et al., *Nature* (London), 382:822–826 (1996)]. The failure of L-1 to activate transcription seems most likely to have resulted from intracellular proteolysis. The nuclear extracts used in vitro transcription assays almost certainly contain proteases as well; however, these are presumably rendered inactive by the proteases inhibitors included in the assays.

The results described herein show that an approximately 4 kDa synthetic molecule containing two linked binding elements, one that targets a DNA-binding protein and another that targets the transcriptional machinery, can coactivate transcription of a mammalian promoter. Specifically, it has been shown that a designed coactivator containing a nonnatural completely D configured peptide stimulates transcription in vitro with only slightly less potency than the corresponding coactivator bearing the natural L configuration. Strikingly, the nonnatural molecule D-1 also stimulates transcription of a GAL4-driven promoter in vivo, when present in conjunction with GAL4-FKBP. The examples described herein thus demonstrate both the feasibility of using small molecules to coactivate gene expression in vitro and in vivo, and the ability of completely nonnatural small molecules to serve this function.

The description of possible mechanisms set forth below is not intended to be limiting of the invention. The ability of a D configured peptide to serve as an activation domain raises a number of interesting mechanistic issues, such as whether the L and D peptides contact the same target. As the FK506 portion of either L-1 or D-1 almost certainly interacts much more strongly with its target than does the activator peptide portion, it is conceivable that the synthetic coactivators first form a stable complex with the GAL4-FKBP fusion protein, and the resulting DNA-bound complex then recruits the transcriptional machinery to the promoter through direct peptide-protein contacts. The target of the L activator peptide is likely to be TFIIB, if indeed it contacts the same protein as the N-terminal portion of the VP16 activation domain, from which the 29-mer is derived [Seipel, K., et al., *EMBO J.*, 11:4961–4968 (1992); Lin, Y. -S, et al., *Nature* (London), 353:569–571 (1991)]. Regardless whether the peptide is fused directly to a DNA-binding domain or bound noncovalently through the aegis of FK506-FKBP interactions, the target of the L peptide probably remains the same. No high-resolution structural information is available for any activation domain bound to its target. However, it has recently been demonstrated that an activation peptide derived from the C-terminal domain of VP16 folds into an a-helix upon interaction with its target. TAFπ3 1, with nonpolar contacts being made by hydrophobic amino acid side-chains that lie among one face of the helix, including one key contact made by a phenylalanine residue that apparently represents a common feature of several acidic activation domains [Uesugi, M., et al., Science, in press (1997)]. It is noted that the repeated sequence in the activation peptide not only contains a Phe residue that is known to serve as important functional role in the intact VP16 activation domain [Cress, W. D. and Triezenberg, S. J., Science, 251:87–90 (1991)], but also contains additional hydrophobic residues at the i+3 and i+4 and i+5 positions, which would all lie along one face of a putative α-helix. If indeed the L peptide contacts its transcriptional target using these residues, it is conceivable that the D peptide could make similar contacts, (though in reversed orientation with respect to the target), because the indicated nonpolar residues would all lie along one face of a D helix, and hydrophobic interactions can exhibit remarkable steric and geometric plasticity. Consistent with this notion, L and D configured calmodulin-binding peptides having the same amino acid sequence bind with similar strength to calmodulin [Fisher, P. J., et al., Nature (London), 368:651–653 (1994). Of course, it remains a real possibility that the L-1 and D-1 target different components of the transcriptional apparatus.

The present demonstration that a nonnatural entity can activate transcription, together with prior findings that activators arise at a small but significant frequency in libraries of random fusion peptides [Ma, J. and Plashne, M., Cell, 51:113–119 (1980)], indicates that it is possible to identify activation domains with low molecular weight from combinatorial libraries of organic molecules. A major limitation to any such screening effort has been the requirement that a prospective activator be physically associated with a DNA-binding domain. The system described herein provides a means of overcoming this limitation by linking the activator to a membrane-permeant organic ligand, e.g., FK506.

Example III
Preparation Of A Combinatorial Test Compound Library

A library of test compounds is prepared as follows:

Resin beads (Merrifield resin) are divided into 5 aliquots, and each aliquot is placed in a reaction vessel of an automatic peptide synthesizer. To each reaction vessel is added one of 5 9-fluorenylmethoxycarbonyl-(Fmoc) protected amino acids (available from, e.g., Sigma Chemical, St. Louis, Mont.), and the protected amino acids are allowed to react with the resin to provide amino acid-derivatized resins. The aliquots are then washed to remove excess reagents and impurities. Each aliquot is treated with piperidine to remove the Fmoc protecting group and the beads are again washed to remove reagents and impurities. Each aliquot of beads is further divided into five aliquots, and each aliquot is treated with an Fmoc-protected pentafluorophenyl amino acid ester (Sigma). After reaction, the beads are washed to remove impurities, and again deprotected and split into five further aliquots, each of which is treated with one of five activated amino acids. After reaction, washing, and deprotection, a library of 125 tripeptides is obtained. Each of the tripeptides is then coupled (at the N-terminus) to a tandemly repeated undecamer sequence derived from the N-terminal of the VP16 activation domain, as described herein. Each peptide is then treated with an activated ester of cysteine to provide an N-terminal cysteine residue. The resulting resin-bound library includes 125 peptides differing at the C-terminal tripeptide.

The resin-bound peptide library is then coupled to a bromoacetylated derivative of FK506 (e.g., as described herein) to provide a library of test compounds having an FK506 portion and a test transcriptional modulating portion. These test compounds are then screened to determine the effect of C-terminal substitution on the transcriptional modulating activity of the peptide and transcriptional modulators are identified.

Example IV
Preparation of a Combinatorial Test Compound Library
General Techniques All reactions were carried out under an argon atmosphere with dry, freshly—distilled solvents under anhydrous conditions, unless otherwise noted. Tetrahydrofuran (THF) and diethyl ether (Et2O) were distilled from sodium-benzophenone, and methylene chloride was distilled from calcium hydride. Yields refer to chromatographically and spectroscopically (1H NMR) homogenous materials, unless otherwise stated.

All reactions were monitored by thin-layer chromatography carried out on 0.25 mm E. Merck silica gel plates (60F-254) using UV light, 2.4% phosphomolybdic acid/ 1.4% phosphoric acid/5% sulferic acid in water or 0.2% ninhydrin in ethanol and heat as developing agents. TSI silica gel (230–400 mesh) was used for flash column chromatography. Preparative thin-layer chromatography (PTLC) seperations were carried out on 0.50 mm E. Merck silica gel plates (60F-254).

NMR spectra were recorded on a Brucker AMX-400 instument and calibrated using tetramethylsilane as an internal reference. The following abbreviations are used to indicate the multiplicities: s, singlet; d, doublet; t, triplet; q, quartet; m, multiplet; b, broad. IR spectra were recorded on a Perkin -Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions.

The following common abbreviations are used: EtOAc: ethyl acetate; TBS: tert-butyldimethylsilyl; Me: methyl; Et: ethyl; Ph: phenyl; Ac: acetyl; Phth: phthaloyl; [4]NBS: 4-nitrobenzenesulfonyl; Bu: butyl.

Although the reaction schemes below indicate single stereoisomers, their enantiomers have been made also.

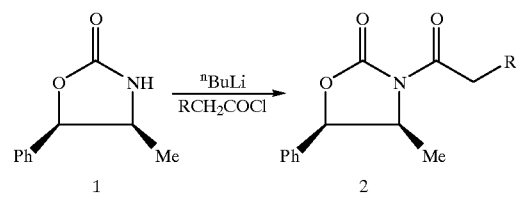

Imide 2. A solution of oxazolidone 1 (7.088 g, 40.00 mmol) in THF (80 mL) was cooled to −78° C. and treated with n-butyllithium (26.3 mL, 1.6 M in hexanes; 1.05 eq). After stirring at the same temperature for 10 min, an acid chloride (46.00 mmol; 1.15. eq) was added to the solution and the resulting solution was warmed to 23° C. over 30 min. The reaction mixture was then quenched with saturated aqueous NaHCO3 (80 mL) and concentrated in vacuo to remove the organic solvents. The resulting aqueous residue was extracted with Et2O (200 mL×2) and the combined organic layers were washed with water (100 mL×1) and brine (100 mnL x 1), and then dried over Na2SO4, filtered and concentrated. Purification of the residue by column chromatography (silica gel, 10→20% EtOAc in hexanes) afforded imide 2 (quantitative yield) as an oil.

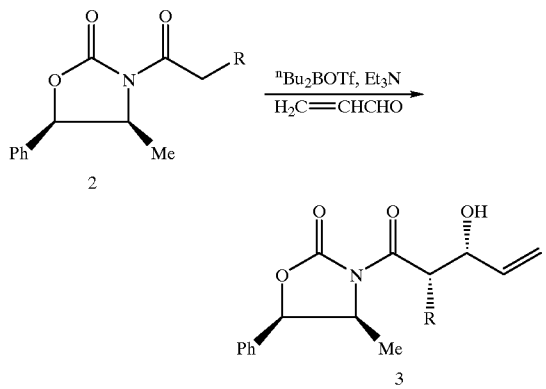

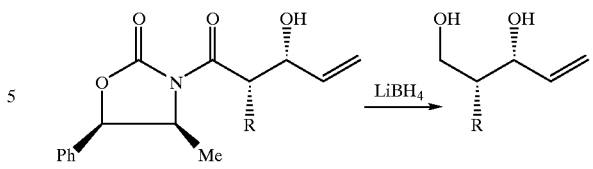

Allyl alcohol 3. A solution of imide 2 (40.00 mmol) in CH$_2$Cl$_2$ (80 mL) was treated with di-n-butylboron trifluoromethanesulfonate (42.0 mL, 1.0 M in CH$_2$Cl$_2$; 1.05 eq) at 0° C. After stirring at the same temperature for 20 min., diisopropylethylamine (7.66 mL, 44.0 mmol) was added dropwise to the solution. After stirring at 0° C. for 20 min, the resulting mixture was cooled to −78° C. Acrolein (4.81 mL, 72.0 mmol), which had been passed through a pad of neutral alumina, was added to the solution and the mixture stirred at −78° C. for 20 min followed by 0° C. for 20 min. The mixture was then quenched with phosphate buffer (60 mL; pH=7.0) and methanol (300 mL), followed by 30% H$_2$O$_2$ (40 mL) at 0° C. After stirring for 1 hr at 0° C., the organic solvents were removed in vacuo. The resulting aqueous residue was extracted with EtOAc (200 mL×2), and the combined organic layers were washed with saturated aqueous NH$_4$Cl/30% NH$_3$ (5:1, 200 mL), brine (100 mL), dried over Na$_2$SO4, filtered and concentrated. Purification of the residue by column chromatography (40 cc of silica gel per 1 g of the residue, 10–25% EtOAc in hexanes) afforded allyl alcohol 3 (67%) as an oil.

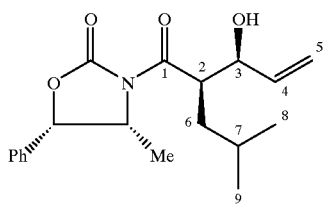

Rf=0.32 (30% EtOAc in hexanes); $[\alpha]^{23}_D$+18.2°(c=1.1, CHCl$_3$); IR (thin film):$\gamma_{max}$=3481 (broad, OH), 2957, 2933, 2871, 1780 (C=O), 1698 (C=O), 1384, 1368, 1221, 1197, 1118 cm$^{-1}$, $^1$HNMR(400 MHz, CDCl$_3$, 23° C.):δ=7.45–7.35 (m, 3H, Ph), 7.31 (m, 2H, Ph), 5.92 (ddd, IH, J=17.2, 10.6, 5.2 Hz, C$_4$-H), 5.66 (d, 1H, J=6.9 Hz, PhCR), 5.32 (ddd, 1H, J=17.2, 1.1, 1.1 Hz, C$_5$-H$_{cis}$), 5.24 (ddd, 1H, J=10.6, 1.1,1.1 Hz, C$_5$-H$_{trans}$), 4.83 (dq, 1H, J=6.9, 1.1 Hz, NCH), 4.31–4.37 (m, 2H, C$_2$-H and C$_3$-H), 2.28 (d, 1H, J=3.1 Hz, OH), 1.81 (ddd, 1H, J=13.3, 10.0, 5.4 Hz, C$_6$-H),1.53 (m, 1H, C$_7$-H), 1.39 (ddd, 1H, J=13.3, 8.6, 3.0 Hz, C$_6$-H'), 0.92 (d, 3H, J=6.9 Hz, NCHCH$_3$), 0.90 (d, 6H,J=6.6 Hz, C$_8$-H$_3$ and C$_8$-H$_3$);$^{13}$C NMR (100 MHZ, CDCl$_3$, 23° C.):δ=174.7, 153.4, 137.3, 133.3, 128.85, 128.76, 125.7, 116.8, 74.5, 55.1, 45.2, 36.4, 26.5, 23.3, 22.2, 11.5; FAB HRMS calcd for C$_{19}$H$_{25}$NO$_4$ (M+NH$_4$)+): 349.2127, found: 349.2135.

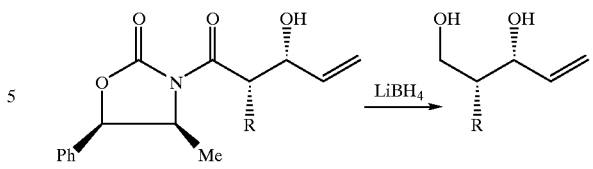

Diol 4. A solution of allyl alcohol 3 (20.00 mmol) in Et$_2$O (70 mL) was treated with lithiurn borohydride (14.0 mL, 2.0 M in THF; 1.4 eq) at 0° C. in the air and stirred at 23° C for 5 min. The reaction mixture was then quenched with saturated aqueous NH$_4$cL (30 mL) and 30% NH$_3$ (10 mL). After stirring for 1 hr at 23° C., the organic solvents were removed in vacuo and the aqueous residue was extracted with EtOAc (100 mL×2). The combined organic layers were then washed with brine (100 mL×1), dried over Na$_2$SO$_4$, filtered and concentrated. Purification of the residue by column chromatography (20 cc of silica gel per 1 mmol, 0.3% MeOH and 30–60% EtOAc in hexanes) afforded diol 4 (90%/o) as an oil and imide 1 (90%) as a solid.

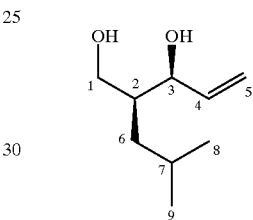

$[\alpha]^{23}_D$-12.9°(c=1.1, CHCl$_3$); IR (thin film):$\gamma_{max}$=3266 (br, OH), 2957, 2871, 1027, 994, 922 cm$^{-1}$; $^1$H NMR (400 MHz, CDCl$_3$, 23° C.):δ=5.95 (ddd, 1H, J=17.1, 10.5, 5.6 Hz, C$_4$-H), 5.32 (ddd, 1H,J-17.1, 1.5, 1.5 Hz, C$_5$-H$_{cis}$), 5.24 (ddd, 1H,J=10.5, 1.5, 1.5 Hz, C$_5$-H$_{trans}$), 4.38 (bd, 1H, C$_3$-H), 3.71 (bm, 2H, C$_1$-H$_2$), 2.56 (d, 1H, J=4.7 Hz, OH), 2.38 (bm, 1H, OH), 1.97 (m, 1H, C$_2$-H), 1.62 (m, 1H, C$_7$-H), 1.15–1.01 (m, 2H, C$_6$-H$_2$), 0.92 (d, 3H, J=6.6 Hz, C$_8$-H$_3$), 0.88 (d, 3H, J=6.6 Hz, C$_8$-H$_3$); $^{13}$C(100 MHz, CDCl$_3$), 23° C.): δ=137.9, 115.8, 76.0, 64.5, 42.1, 35.2, 25.5, 23.2, 22.2; FAB HRMS calcd for C$_9$H$_{18}$NO$_2$ (M+NH$_4$+): 176.1651, found: 176.1657.

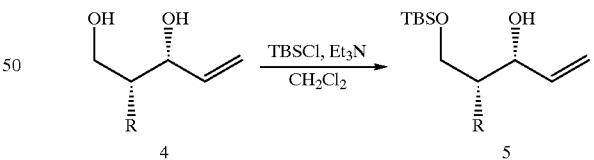

Silyl ether 5. A solution of diol 4 (10.00 mmol) and triethylamine (1.74 mL; 12.5 mmol) in CH$_2$Cl$_2$ (20 mL) was treated with tert-butyldimethylsilyl chloride (1.733 g; 11.5 mmol) at 0° C. and stirred at 23° C. for 8 hr. The reaction mixture was then quenched with phosphate buffer (20 mL; pH=7.0) and concentrated in vacuo to remove the organic solvent. The resulting aqueous residue was extracted with Et$_2$O (100 mL×1) and the organic layer washed with brine (50 mL×1), dried over Na$_2$SO$_4$, filtered and concentrated. Purification of the residue by column chromatography (6.2 cc of silica gel per 1 mimol, 4→8% EtOAc in hexanes) afforded silyl ether 5 (71%) as an oil.

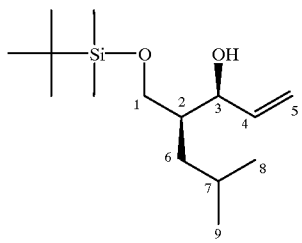

Rf=0.61 (25% EtOAc in hexanes); $[\alpha]^{23}_D$ −45.4°(c=1.1, CHCl$_3$); IR (thin film):$\gamma_{max}$=3400 (br, OH), 2956, 2929, 2900, 2859, 1471, 1255, 1090, 1060, 837 cm$^{-1}$, $^1$H NMR (400 MHz, CDCl$_3$, 23°):δ=5.88 (ddd, 1H, J=17.2, 10.6, 5.2 Hz, C$_4$-H), 5.31 (ddd, J=17.2, 1.8, 1.8 Hz, C$_5$-H$_{cis}$), 5.19 (ddd, 11H, J=10.6, 1.8, 1.8 Hz, C$_5$-H$_{trans}$), 4.30 (bm, 1H, C$_3$-H), 3.74 (d, 1H, J=6.1 Hz, C$_1$-H), 3.69 (d, 1H, J=1.2 Hz, OH), 3.70 (d, 1H, J=9.9Hz, C$_1$-H'), 1.92 (m, 1H, C$_2$-H), 1.58 (m, 1H, C$_2$-H), 1.11–1.05 (m, 2H, (C$_6$-H$_2$), 0.91 (S, 9H, t-Bu), 0.89 (m, 6H, C$_8$-H$_3$ and C$_8$-H$_3$), 0.081 (s, 3, Si Me), 0.076 (s, 3H. SiMe); C13 NMR (100 MHz, CDCL$_3$, 23° C.)δ=138.1, 115.1, 75.8, 65.5, 42.0, 34.9, 25.7, 25.4, 23.2, 22.2, 18.0;

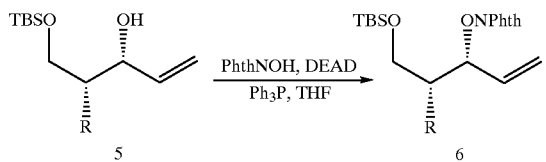

N-Alkoxyphthalimide 6. A solution of silyl ether 5 (1.00 mmol), N-hydroxyphthalimide (196 mg; 1.20 mmol) and triphenylphosphine (315 mg; 1.20 mmol) in THF (6.0 mL) was treated with diethylazodicarboxylate (189 μL; 1.20 mmol) at 0° C. and warmed to 23° C. After stirring at the same temperature for 45 min, the solvent was removed in vacuo and the residue passed through a plug of silica gel eluted with 20% EoOAc in hexanes. The elute was concentrated and the residue purified by column chromatography (60 cc of silica gel per 1 g of the residue, 5% EtOAc in hexanes) to afford N-alkoxyphthalimide 6 (67%) as an oil.

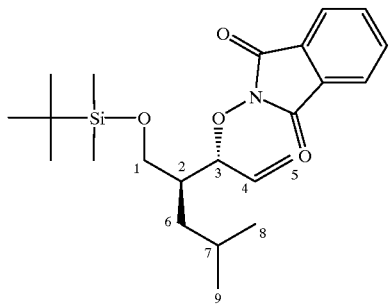

Rf=0.68 (25% EtOAc in hexanes); $^1$H NMR (400 MHz, CDCl$_3$, 23° C.):δ=7.80 (m,2H),(Ar), 7.71 (m, 2H, Ar), 5.96 (ddd, 1H, J=17.0, 10.1, 10.1 Hz, C$_5$-H), 5.24 (dd, 1H J=10.1, 1.6 Hz, C$_5$-H$_{trans}$), 5.18 (dd, 1H, J=17.0, 1.5 Hz, C$_5$-H$_{cis}$), 4.81 (dd, 1H, J=9.7 6.1 Hz, C$_3$-H), 3.80 (dd, 1H, J=10.1, 4.4 Hz, C$_1$-H), 3.60 (dd, 1H, J=10.1, 6.2, C$_1$-H') 2.13 (m, 1H, C$_2$-H), 1.76 (m, 1H, C$_2$-H), 1.33–1.25 (m, 2H, C$_6$-H$_2$), 0.93, 0.93 (d, 3H×2, J=4.8 Hz, C$_8$-H$_3$ and C$_8$-H$_3$), 0.92 (s, 9H, t-Bu) 0.10 (s, 3H, Si—Me), 0.06 (s, 3H, Si—Me); $^{13}$C NMR (100 MHz, CDCl$_3$, 23° C.):δ=;FAB HRMS calcd for C$_{23}$H$_{39}$N$_2$O$_4$Si (M+NH$^{4+}$): 435.2683, found: 435:2683.

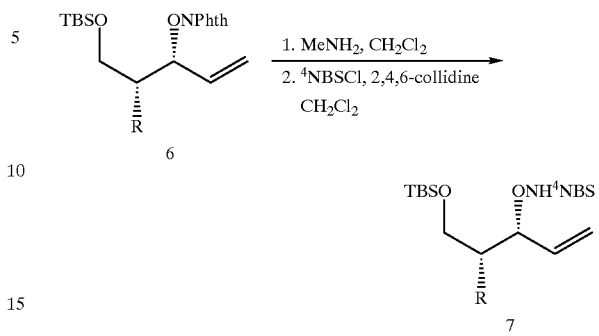

N-Alkoxysulfonamide 7. A solution of N-alkoxyphthalimide 6 (1.00 mmol) in CH$_2$Cl$_2$ (4.0 mL) was treated with methylamine (0.38 mL, 8.0 M in EtOH; 3.0 eq) and stirred at 23° C. for 15 min in the air. The solvents were then removed in vacuo and the residue was azeotroped with benzene 3 times to remove methylamine. The residue was dissolved in CH$_2$Cl$_2$ (4.0 mL) and 2,4,6-collidine (172 μL; 1.3 mmol) was added to the solution. The resulting mixture was cooled to 0° C. and treated with 4-nitrobenzenesulfonyl chloride (266 mg, 1.2 mmol). After stirring at the same temperature for 15 min, the reaction mixture was quenched with diethylamine (10 μL; 0.1 rmmol) and then poured into EtOAc (20 mL). The organic layer was washed with aqueous KHSO$_4$, (10 mL, 0.1 M) and then brine, dried over Na$_2$SO4, filtered and concentrated. Purification of the residue by column chromatography (45 cc of silica gel per 1 mmnol, 7→15% EtOAc in hexanes) afforded N-Alkoxysulfonamide 7 (98%) as an oil.

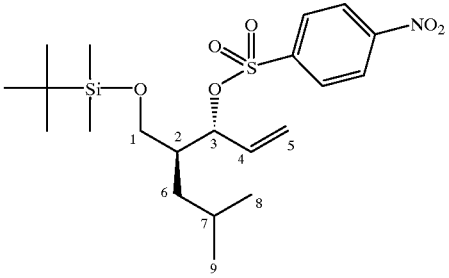

Rf0.50 (20% EtOAc in hexanes); $[\alpha]^{23}_D$-45.4°(c=1.1, CDCl$_3$); IR (thin film): $\gamma_{max}$=3400 (br, O—H; $^1$H NMR (400 MHz, CDCl$_3$, 23° C.):δ=8.39 (ddd, 2H, 8.9, 2.0, 2.0 Hz, Ar), 8.13 (ddd, 2H, 8.9, 2.0, 2.0 Hz, Ar), 7.03 (s, 1H, NH), 5.71 (ddd, 1H, J=17.1, 10.0, 8.5 Hz, C$_4$-H), 5.32 (d, 1H, J=10.0 Hz, C$_8$-H$_{trans}$), 5.29 (d, J=17.1 Hz, C$_8$-H$_{cis}$), 4.51 (dd, 1H,J=8.3, 5.6 Hz, C$_3$-H), 3.55 (dd, 1H,J=10.3 4.6 Hz, C$_1$-H), 3.42 (dd, 1H,J=10.3, 7.1 Hz, C$_1$-H'), 1.91 (m, 1H, C$_2$-H), 1.59 (m, 1H, C$_7$-H), 1.07–1.03 (m, 2H, C$_6$-H$_2$) 0.88 (s, 9H, t-Bu), 0.85 (d, 3H, J=6.4 Hz, C$_8$-H$_3$), MHz, CDCl$_3$, 23° C.); FAB HRMS calcd for C$_{21}$H$_{40}$N$_3$SO$_6$Si (M+NH$_4^+$): 490.2407, found: 490.2430.

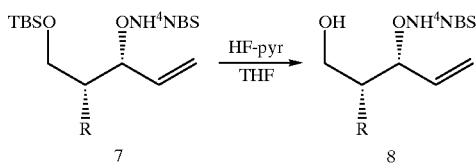

Alcohol 8. A solution of N-Alkoxysulfonamide 7 (1.00 mmol) in THF (5.0 mL) in a polypropylene vessel was treated with HF-pyridine (0.6 mL) at 0° C. and stirred at 23° C. for 10 hr. The reaction mixture was diluted with Et$_2$O (5mL) and quenched with saturated NaHCO$_3$ solution until bubbling ceases. After removal of the organic solvents in vacuo, the resulting aqueous residue was extracted with EtOAc (50 mL×2). The combined organic layers were washed with aqueous KHSO$_4$ (50 mL, 0.1 M) water and brine, and then dried over Na$_2$SO$_4$, filtered and concentrated. Purification of the residue by column chromatography (45 cc of silica gel per 1 mmol, 0.2% MeOH and 20→30% EtOAc in hexanes) afforded alcohol 8 (65%) as a white solid. The product was stored at −20° C. for a prolonged period of time.

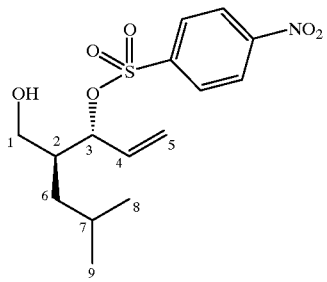

Rf=; $^1$H NMR (400 MHz, CDCl$_3$, 23° C.): δ=8.43 (d, 2H, J=9.0 Hz, Ar), 8.14 (d, 2H, J=9.0, Ar), 7.13 (s, 1H, NH), 5.65 (ddd, J=17.7, 9.0, 9.0 Hz, C$_4$-H), 4.38 (dd, 1H, J=9.0, 9.0 Hz, C$_3$-H), 3.78 (m, 1H, C$_1$-H), 3.56 (m, 1H, C$_1$-H'), 2.00 (m, 1H, O—H), 1.68 (m, 1H, C$_2$-H), 1.34–1.25 (m, 2H, C$_6$-H$_2$), 0.97.(m, 1H, C$_7$-H), 0.89 (d, 3H, J=6.6 Hz, C$_8$-H$_3$), 0.82 (d, 3H, 6.5 Hz, C$_9$-H$_3$) $^{13}$C NMR (100 MHz, CDCl$_3$, 23° C.):δ=150.8, 142.6, 134.4, 129.7, 124.4, 121.7, 90.3, 61.3, 41.3, 35.8, 25.3, 23.6, 21.7; IR (film) cm 3400 (br, O—H); [α]$_{23}^D$-45.4°(c=1.1, CDCl$_3$).

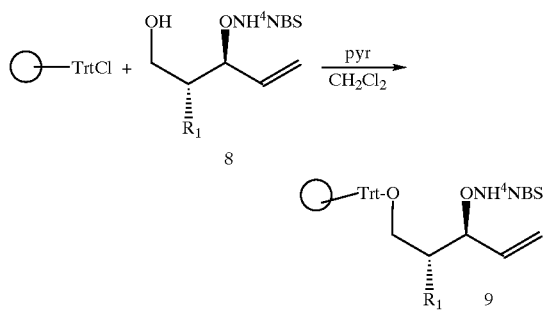

Figure 4A:
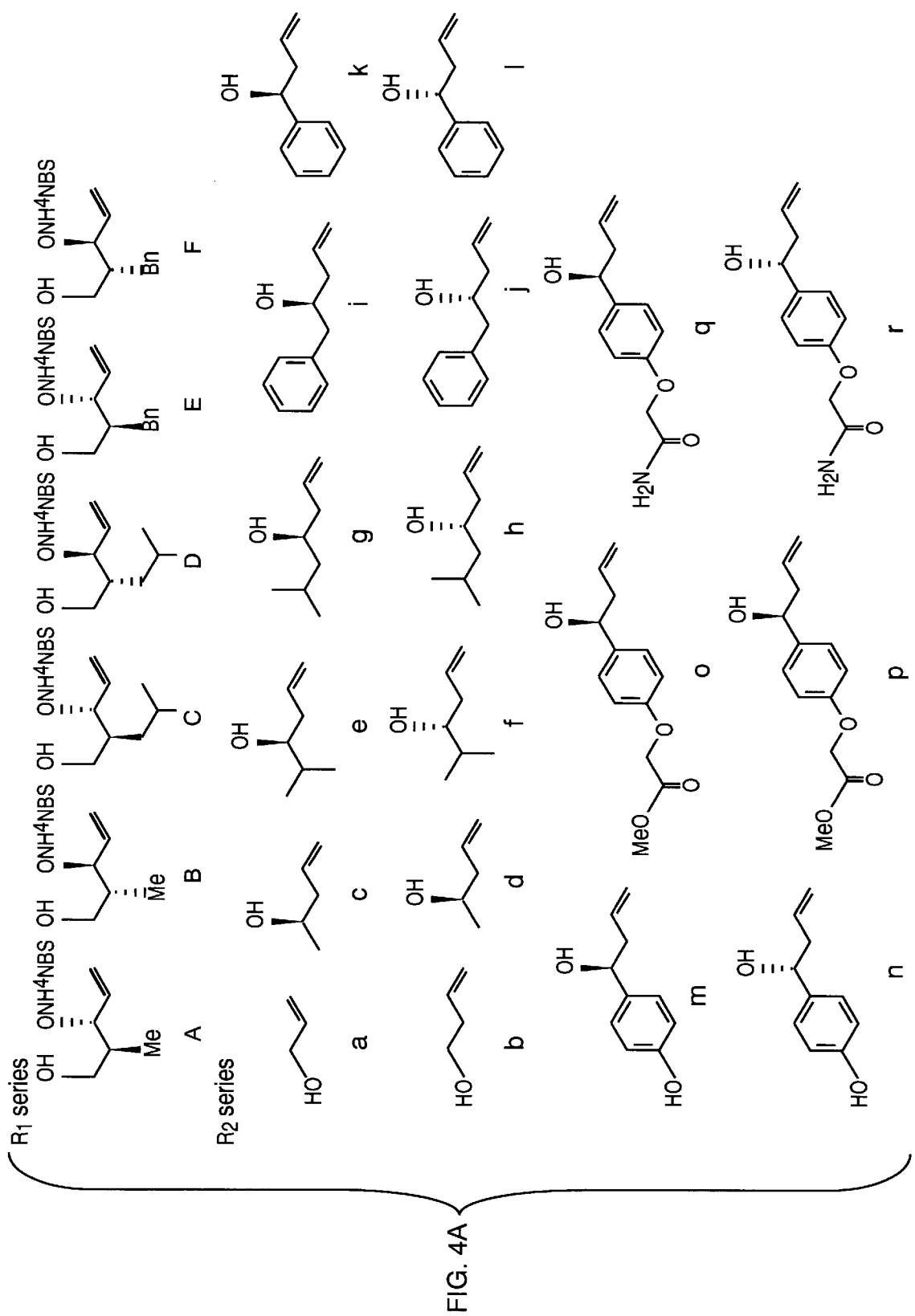
FIG. 4 is a chart of monomers used in the combinatorial library for Example 4.
Figure 4B:
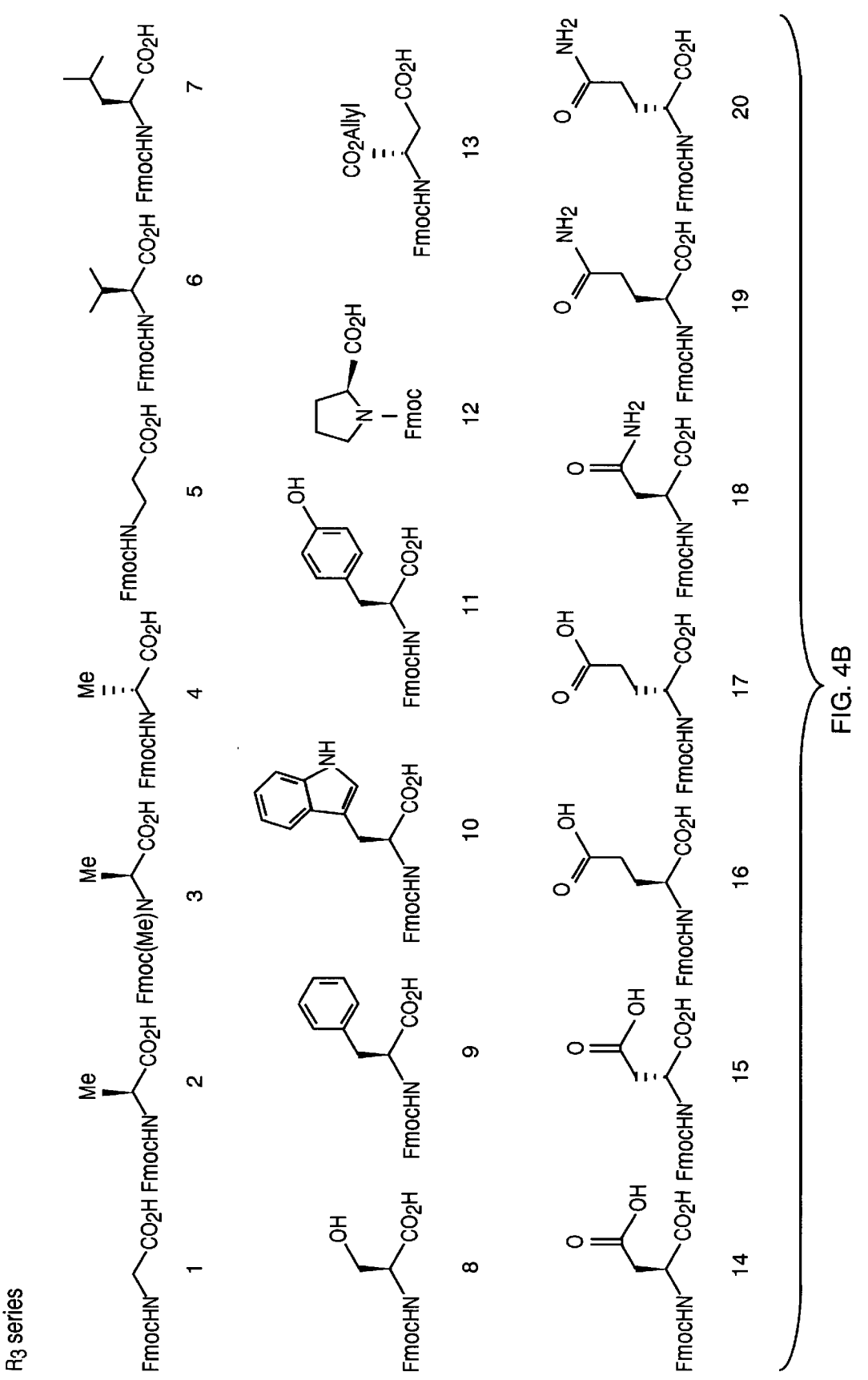

N-Alkoxysulfonamide 9: A combinatorial library of test compounds was prepared using the following procedure. The reaction was repeated six times with six alcohols, each with a different R$_1$ group (FIG. 4). Resin beads (polystyrene resin, 1.70 g, 2.05 mmol), alcohol (8, 0.72 mmol) and pyridine (1.41 mL; 17.43 nunol) were stirred together under argon at room temperature for 45 hours. Five equivalents of methanol (0.71 mL) were then added to the reaction mixture. It was then shaken for eleven hours. The resin was subsequently rinsed with dimethylformamide (DMF) followed by dichloromethane. The resin was then divided into 18 90 mg portions, and each portion was placed in a separate vessel.

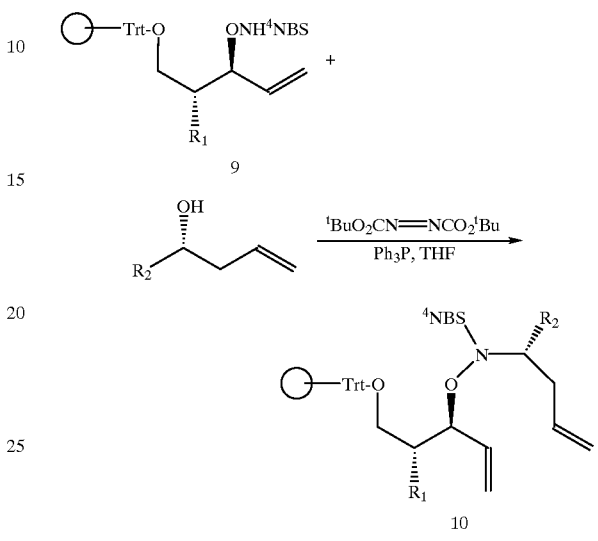

N-Alkoxysulfonamide 10: The reaction was carried out with each of the eighteen different R$_2$ alcohols shown in FIG. 4. For the benzylic and allylic homoallyl alcohols, the following procedure was used. Three equivalents of alcohol (0.72 mmol) was dissolved in 1.89 mL of THF under argon with 198.3 mg (0.756 mmol) of triphenylphosphine. A second solution of tBuO$_2$CN=NCO$_2$tBu (174.1 mg, 0.756 mmol) in THF (1.89 mL) was prepared under argon. One sixth of the alcohol solution was added to the resin at room temperature, and the mixture was subsequently chilled to −50° C. One-sixth of the second solution was then added, and the resulting mixture was shaken for thirty minutes at room temperature.

For aliphatic alcohols, the following procedure was used. The aliphatic alcohol (1.80 mmol) was added directly to a 0° C. solution of tBuO$_2$CN=NCO$_2$tBu (230.3 mg, 1.89 mmol) and triphenylphosphine (495.7 mg, 1.89 mmol) in 3.60 mL of THF. The solution was then stirred for two minutes before being added to the resin. The reaction mixture was then shaken for 12 hours at room temperature before being washed twice with DMF and thrice with dichloromethane.

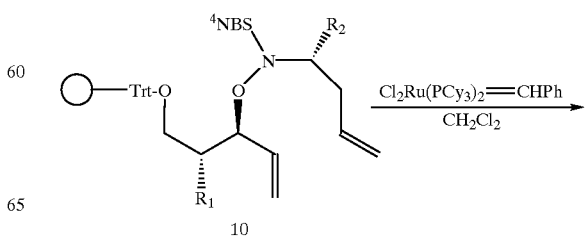

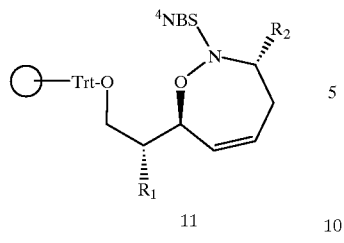

11

Tetrahydroxazepine 11: 889 mgs of Ru catalyst was dissolved in 72 mL of degassed dichloromethane. To each of the 108 compounds formed by the previous reaction, 0.65 mL of this solution was added at room temperature. The resulting reaction mixtures were then stirred for one hour and the process was repeated once.

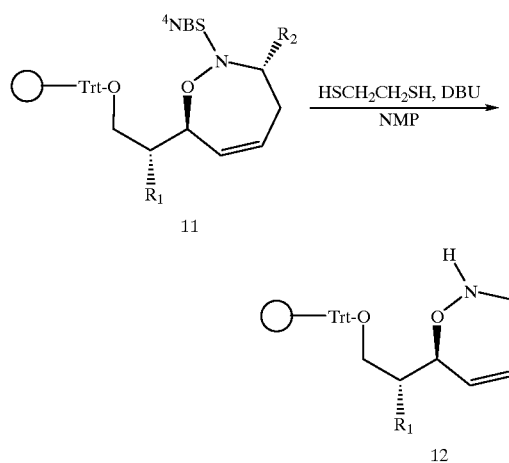

Tetrahydroxazepine 12: A solution of ethanedithiol (4.82 mL; 57.5 mmol) and 1,8-diazabicyclo[5,4]undec-7-ene (DBU, 4.30 Ml; 28.8 mmol) was made in 108 mL of 1-methyl-2-pyrrolidinone (NMP) under nitrogen at 0° C. 1.0 niL of this solution was then added to each of the 108 reaction vessels at room temperature and stirred for fifteen minutes. The resin was then washed with DMF twice and dichloromethane thrice. The same procedure was then repeated once.

A slurry of the resin was then prepared in 4.5 mL of 35% dichloromethane in NMP and divided into 20 pipet tips (1–20 μL beveled filter tip). The residual resin was then prepared in the same manner and divided between the 20 pipet tips. All the resin was then washed with THF twice, flushed with nitrogen and dried under vacuum.

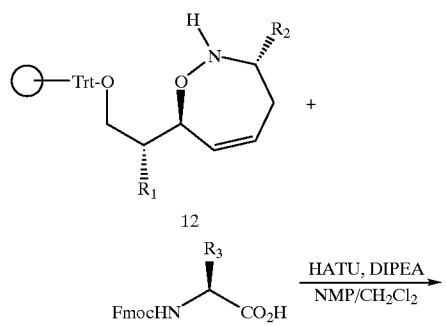

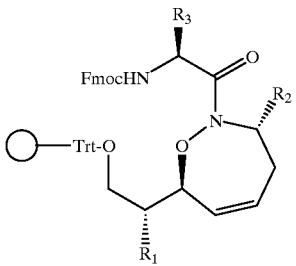

13

Protected Amine 13: The reaction was done with the 20 amino acids shown in FIG. 4, bringing the total number of compounds in the library to 2160. The amino acid (1.652 mmol) and HATU (O-(7-azabenzotriazol-1-yl)- 1,1,2,2-tetramethyluronium; 628 mg, 1.652 mmol) were dissolved in 50% dichloromethane in NMP (8.26 mL). Diisopropyl-ethylamine (0.576 Ml 3.304 mmol) was then added to the solution at 0° C. 70 μL of the resulting solution was added to each reaction vessel and shaken at room temperature. After one hour, the resin was rinsed with 50% dichol-romethane in NMP three times followed by 30% dichloromethane in NMP once.

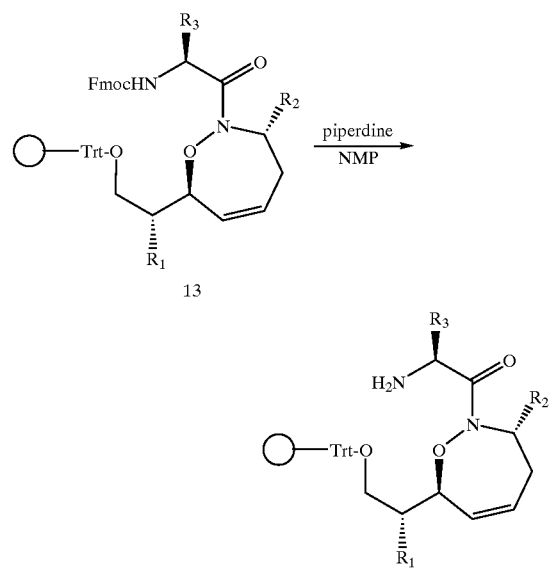

Amine 14: To deprotect the amino group, a solution of 20% piperdine in NMP was prepared and 105 μL of the solution was added to each vessel at room temperature. The resin was then rinsed with dichloromethane three times and dried in vacuo.

The resulting small molecule library was then coupled to the FK506 analog. HATU (5.1738 g; 13,61 mmol) and the FK506 analog (7.9427 g; 13.61 mmaol) were dissolved in 65 mL of dichloromethane and 86 mL of NMP at room temperature. Diisopropylethylamine (4.74 mL; 27.22 mmol) was added to the solution. The solution was then added to each of the reaction vessels containing the resin in 75 μL portions. The resulting mixtures were stirred for six hours at room temperature. Then, the resin was rinsed with acetonirile three times and the eluant was collected. The resin was subsequently rinsed with 300 μL of DMF twice, 300 μL of 1:1 dichloromethane:DMF twice, and 300 μL of dichloromethane thrice. 6.598 g of the FK506 analog was recovered after an aqueous work up and column chromatography.

The resulting library of compounds were cleaved from the resin with either 1% trifluoroacetic acid and 5% isopropylsilyl hydride in dichloromethane (for compounds containing the following $R_3$ moieties: 1–9, 12, 13, and 18–20) or 20% trifluoroacetic acid and 5% isopropylsilyl hydride, in dichloromethane (for compounds with $R_3$ moieties of 10, 11, and 14–17). In vivo Assay for Transcriptional Modulating Activity: Jurkat cells were transiently transfected with the plasmids described in FIG. 4A of Nyanguile et al. (PNAS (1997) 94:13402–13406; the contents of which is expressly incorporated herein by reference). After 20 hour incubation, the medium was removed and the cells were resuspended in 1% (v/v) penicillin/streptomycin and 10% (v/v) fetal bovine serum in RPMI and aliquotted into the 96-well microtitre plate (100 μL, 1×10$^6$ cells per well). 0.8 μL of dimethylsulfoxide (DMSO) solution containing a library compound was added to each well and the plates were incubated for 48 hours at 37° C. Secreted alkaline phosphatase (SEAP) activity was measured as described in Nyanguile et al.

HL2Fr3 cells were transfected with the 1st and 3rd genes described in FIG. 1C of Rivera et al (Nature Medicine 1996 2:1028–1032; the contents of which is expressly incorporated herein by reference). The cells were resuspended in 1% (v/v) penicillin/streptomycin and 10% (v/v) fetal bovine serum in minimal essential medium and aliquotted into the 96 well microtitre plate (200 μL, 2×10$^4$ cells per well). 0.8 μL of DMSO solution containing a library compound was added to each well and the plates Iwere incubated for 48 hours at 37° C. SEAP activity was measured as described in Nyanguile et al.

Figure 5:
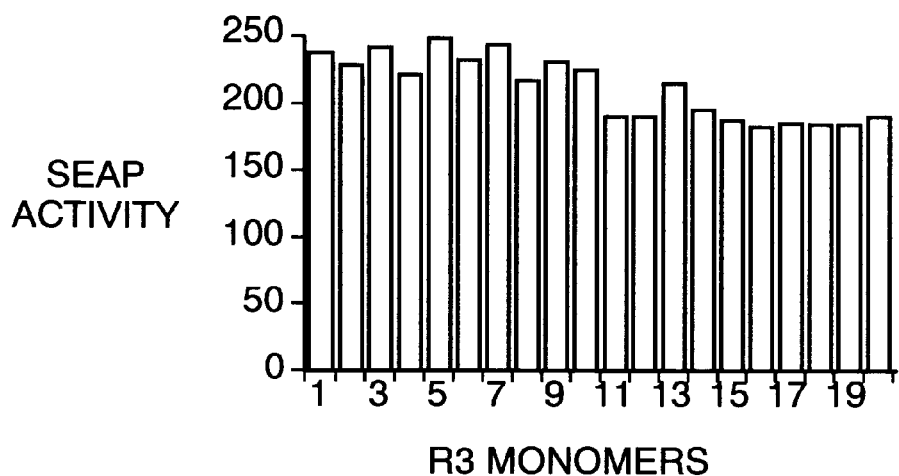
FIG. 5 is a bar graph of the average transcriptional modulating activities for each compound of the combinatorial library with a given R3 monomer.
Figure 6:
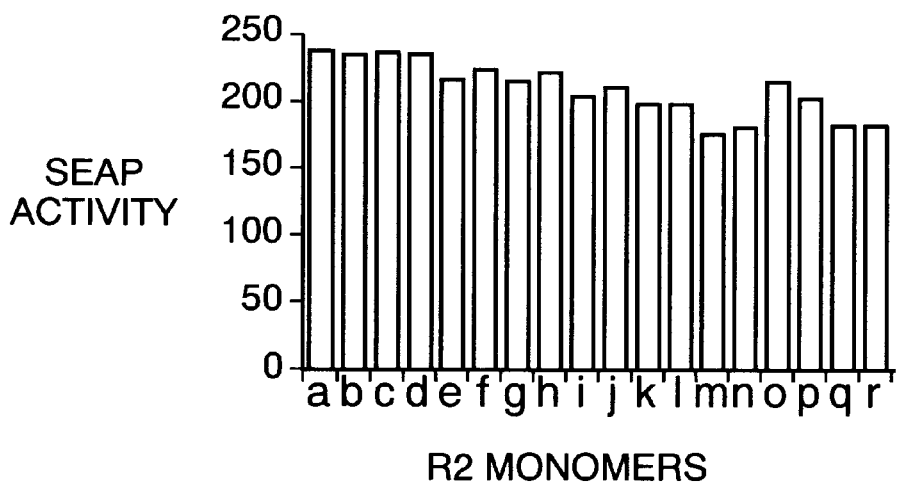
FIG. 6 is a bar graph of the average transcriptional modulating activities for each compound of the combinatorial library with a given R2 monomer.

In FIG. 5, the SEAP activities of the R3 series of library compounds are shown. For each monomer of the R3 series, an average was taken for all the library compounds containing that monomer. The graph shows that library compounds that contain R3 monomers such as 1, 3, 5, 6 and 9 are active tmnscriptional modulators. Similarly, in FIG. 6, the average SEAP activities are displayed for each monomer of the R2 series. For this series, library compounds that show transcriptional modulating activity include compounds which contain R2 monomers a, b, c, d, f and h.

The contents of all cited references (including literature references, issued patents, published patent applications, and co-pending patent applications) cited throughout this application (including the Background Section) are hereby expressly incorporated by reference. The entire contents of Appendix A entitled "A Nonnatural Transcriptional Coactivator" also is incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for modulating expression of a target gene in a cell, comprising: contacting a cell comprising (i) a genetic construct encoding a chimeric protein which comprises at least one ligand-binding domain and a DNA-binding domain which is heterologous thereto, wherein the ligand-binding domain binds to a selected ligand, and (ii) a target gene under the control of at least one transcriptional regulatory element which is recognized by the DNA-binding domain of the chimeric protein with a transcriptional modulator which comprises the selected ligand linked to a transcription modulating portion under conditions which allow transcription of the target gene, such that expression of the target gene is modulated.

2. The method of claim 1, wherein the transcriptional modulating portion is a chemical moiety.

3. The method of claim 1, wherein the transcriptional modulating portion is a proteinaceous domain.

4. The method of claim 1, wherein the chimeric protein is in the nucleus of the cell.

5. The method of claim 1, wherein the chimeric protein is in the cytoplasm of the cell.

6. The method of claim 1, wherein the selected ligand has a molecular weight of less than about 3 kD.

7. The method of claim 1, wherein the selected ligand has a molecular weight of less than about 1.5 kD.

8. The method of claim 1, wherein the selected ligand and the transcriptional modulating portion of the transcriptional modulator are covalently linked.

9. The method of claim 1, wherein the target gene is selected from the group consisting of a gene encoding a protein conferring resistance to a drug, a gene encoding an enzyme, a gene which rescues an autotrophic phenotype, and a gene encoding a cell surface antigen.

10. The method of claim 1, which results in activation of transcription of the target gene.

11. The method of claim 1, which results in inhibition of transcription of the target gene.

12. The method of claim 1, wherein the cell is a mammalian cell.

13. The method of claim 1, wherein the cell is cultured in vitro in culture medium and the contacting step is effected by adding the transcriptional modulator to the culture medium.

14. The method of claim 1, wherein the cell is in a subject and the contacting is effected by administering the transcriptional modulator to the subject.

15. The method of claim 1, wherein the target gene encodes a protein selected from the group consisting of a growth or a differentiation factor, a protein involved in clotting or thrombolysis, a protein involved in promoting or inhibiting vascularization, a protein involved in metabolic regulation, an enzyme, and a tumor suppressor.

16. The method of claim 1, wherein the transcriptional modulator contains at least one D-amino acid.

17. The method of claim 2, wherein the transcriptional modulator is membrane-permeant.

18. The method of claim 2, wherein the transcriptional modulator has a molecular weight of less than about 3 kDa.

19. The method of claim 2, wherein the selected ligand is selected from the group consisting of FK506, FK520, rapamycin, cyclosporin A, tetracycline, steroid, and derivatives thereof.

20. The method of claim wherein the ligand-binding domain of the chimeric protein comprises between about 50 and 350 amino acids.

21. The method of claim 2, wherein the ligand-binding domain of the chimeric protein is less than about 200 amino acid residues in length.

22. The method of claim 2, wherein the ligand-binding domain of the chimeric protein binds to the ligandThw an affinity of less than or equal to about $10^{-6}$ M.

23. The method of claim 2, wherein the ligand-binding domain of the chimeric protein comprises an iumunophilin domain, a cyclophilin domain, a steroid binding domain, an antibiotic domain, an antibody domain, a dihydrofolate reductase (DHFR) domain, or a DNA gyrase domain.

24. The method of claim 2, wherein the ligand-binding domain comprises an FK506 binding protein (FKBP) 12 or a variant thereof which is modified to have a higher binding affinity for the selected ligand compared to an unmodified form.

25. The method of claim 2, wherein the DNA-binding domain is selected from the group consisting of a homeodomain, and a zinc finger domain.

26. The method of claim 9, wherein the target gene encodes a protein which provides for calorimetric, luminescent or fluorescent detection.

27. The method of claim 12, wherein the cell is a human cell.

28. The method of claim 12, wherein the cell is of a cell type selected from the group consisting of a hematopoietic cell, a neural cell, a mesenchymal cell, a cutaneous cell, a mucosal cell, a stromal cell, a muscle cell, a spleen cell, a reticuloendothelial cell, an epithelial cell, an endothelial cell, a hepatic cell, a renal cell, a gastrointestinal cell, and a pulmonary cell.

29. The method of claim 15, wherein the growth or differentiation factor is a hematopoietic or a neurotrophic factor.

30. The method of claim 15, wherein the protein is erythropoietin, growth hormone or an interferon.

31. The method of claim 24, wherein the FKBP12 variant comprises up to 10 amino acid substitutions relative to wild-type FKBP.

32. The method of claim 24, wherein the FKBP12 variant comprises one or more substitutions of Tyr 26, Phe 36, Asp 37, Tyr 82 and Phe 99 with a different amino acid.

33. The method of claim 24, wherein the FKBP12 is encoded by a nucleotide sequence which selectively hybridizes to a nucleotide sequence encoding an FKBP or a variant thereof.

34. The method of claim 28, wherein the cell is a muscle cell.

35. A method for modulating expression of a target gene in a cell, comprising: contacting a cell comprising a genetic construct encoding a chimeric protein which comprises at least one ligand-binding domain and a DNA-binding domain which is heterologous thereto, wherein the ligand-binding domain binds to a selected ligand and the DNA-binding domain binds to a target gene under the control of at least one transcriptional regulatory element which is recognized by the DNA-binding domain of the chimeric protein with a transcriptional modulator which comprises the selected ligand linked to a transcription modulating portion under conditions which allow transcription of the target gene, such that expression of the target gene is modulated.

* * * * *

SEQUENCE LISTING

<160> NUMBER OF SEQ ID NOS: 1

<210> SEQ ID NO 1
<211> LENGTH: 29
<212> TYPE: PRT
<213> ORGANISM: synthetic construct

<400> SEQUENCE: 1

Cys Gly Ser Asp Ala Leu Asp Asp Phe Asp Leu Asp Met Leu Gly Ser
 1               5                  10                  15

Asp Ala Leu Asp Asp Phe Asp Leu Asp Met Leu Gly Ser
            20                  25